US007108969B1

(12) United States Patent
Warrington et al.

(10) Patent No.: US 7,108,969 B1
(45) Date of Patent: Sep. 19, 2006

(54) METHODS FOR DETECTING AND DIAGNOSING ORAL CANCER

(75) Inventors: Janet A. Warrington, Los Altos, CA (US); David T. W. Wong, Newton, MA (US); Charles Randolph Todd, Boxford, MA (US); Mamatha Mahadevappa, Cupertino, CA (US)

(73) Assignees: Affymetrix, Inc., Santa Clara, CA (US); President & Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/950,016

(22) Filed: Sep. 10, 2001

Related U.S. Application Data

(60) Provisional application No. 60/231,057, filed on Sep. 8, 2000.

(51) Int. Cl.
*C12Q 1/68* (2006.01)
*C12P 19/34* (2006.01)
*C12M 1/34* (2006.01)

(52) U.S. Cl. .................. 435/6; 435/91.2; 435/287.2
(58) Field of Classification Search ............... 435/6, 435/91.2, 287.2
See application file for complete search history.

(56) References Cited

U.S. PATENT DOCUMENTS

| | | | |
|---|---|---|---|
| 5,143,854 A | 9/1992 | Pirrung et al. | 436/518 |
| 5,384,261 A | 1/1995 | Winkler et al. | 436/518 |
| 5,424,186 A | 6/1995 | Fodor et al. | 435/6 |
| 5,445,934 A | 8/1995 | Fodor et al. | 435/6 |
| 5,556,752 A | 9/1996 | Lockhart et al. | 435/6 |
| 5,631,734 A | 5/1997 | Stern et al. | 356/317 |
| 5,677,195 A | 10/1997 | Winkler et al. | 436/518 |
| 5,708,153 A | 1/1998 | Dower et al. | 536/22.1 |
| 5,733,729 A | 3/1998 | Lipshutz et al. | 435/6 |
| 5,744,305 A | 4/1998 | Fodor et al. | 435/6 |
| 5,770,358 A | 6/1998 | Dower et al. | 435/6 |
| 5,770,722 A | 6/1998 | Lockhart et al. | 536/25.3 |
| 5,789,162 A | 8/1998 | Dower et al. | 435/6 |
| 5,800,992 A | 9/1998 | Fodor et al. | 435/6 |
| 5,856,174 A | 1/1999 | Lipshutz et al. | 435/286.5 |
| 5,874,219 A | 2/1999 | Rava et al. | 435/6 |
| 5,922,591 A | 7/1999 | Anderson et al. | 435/287.2 |
| 5,962,237 A * | 10/1999 | Ts'o et al. | 435/7.23 |
| 5,981,956 A | 11/1999 | Stern | 250/458.1 |
| 6,013,440 A | 1/2000 | Lipshutz et al. | 435/6 |
| 6,013,449 A | 1/2000 | Hacia et al. | 435/6 |
| 6,025,601 A | 2/2000 | Trulson et al. | 250/461.2 |
| 6,033,850 A | 3/2000 | Purvis | 435/6 |
| 6,040,138 A | 3/2000 | Lockhart et al. | 435/6 |
| 6,040,193 A | 3/2000 | Winkler et al. | 436/180 |
| 6,043,080 A | 3/2000 | Lipshutz et al. | 435/287.2 |
| 6,045,996 A | 4/2000 | Cronin et al. | 435/6 |
| 6,050,719 A | 4/2000 | Winkler et al. | 366/144 |
| 6,171,798 B1 * | 1/2001 | Levine et al. | 435/6 |

OTHER PUBLICATIONS

Chang, D.D. et al. Characterization of transformation related genes in oral cancer cells. Ocnogene 16:1921-1930 (Apr. 1998).*
Ibrahim, S.O. et al. Expression of biomarkers in oropharyngeal squamous cell carcinomas. Oral Oncology 35:302-313 (May 1999).*
Alizadeh et al., "Distinct types of diffuse large B-cell lymphoma identified by gene expression profiling," *Nature*, 403:503-511 (2000).
Alon et al., "Broad patterns of gene expression revealed by clustering analysis of tumor and normal colon tissues probed by oligonucleotide arrays," *Proc. Nat'l. Acad. Sci. U.S.A.*, 96:6745-50 (1999).
Barringer et al., "Blunt-end and single-strang ligations by Escherichia coli ligase: . . . ," *Gene*, 89:117 (1990).
Fodor et al., "Light-Directed, Spatially Addressable Parallel Chemical Synthesis," *Science*, 251:767-772 (Feb. 14, 1991).
Golub et al., "Molecular Classification of Cancer: . . . ," *Science*, 286:531-537 (1999).
Guatelli et al., "Isothermal, *in vitro* amplification of nucleic acids by a multienzyme reaction modeled after retroviral replication," *Proc. Natl. Acad. Sci U.S.A.*, 87:1874-1878 (1990).
Jourenkova-Mironova et al., "Glutathone *S*- Transferase *GSTM1*, *GSTP1*, and *GSTT1* Genotypes . . . ," *Int'l. J. Cancer*, 81:44-48 (1999).
Katoh et al., "Genetic Polymorphisms of Tobacco- and Alcohol-Related Metabolizing Enzymes and Oral Cavity Cancer," *Int'l. J. Cancer*, 83:606-609 (1999).
Kowh et al., "Transcription-based amplification system and detection of amplified human immunodeficiency virus type 1 with a bead-based sandwich hybridization format," *Proc. Natl. Acad. Sci U.S.A.*, 86:1173-1177 (1989).
Landegren et al., "A Ligase-Mediated Gene Detection Technique," *Science*, 241:1077-1080 (1988).
Leethanakul et al., "Gene expression profiles in squamous cell carcinomas of the oral cavity: . . . ," *Oral Oncol.*, 36:474-483 (2000).
Lehninger, *Principles of Biochemistry*, pp. 793-800 (Worth Publishing, 1982).
Lockhart et al., "Expression monitoring by hybridization to high-density oligonucleotide arrays," *Nat'l. Biotechnol.*, 14:1675-1680 (1996).
Luo et al., "Gene expression profiles of laser-captured adjacent neuronal subtypes," *Nature Med.*, 5(1):117-122 (1999).
Mahadevappa and Warrington, "A high-density probe array sample preparation method using 10- to 100-fold fewer cells," *Nat'l. Biotechnol.*, 17:1134-1136 (1999).
Marshall, "Tumor Suppressor Genes," *Cell*, 64:313-326 (1991).

(Continued)

*Primary Examiner*—Diana B. Johannsen
(74) *Attorney, Agent, or Firm*—Banner & Witcoff, Ltd.

(57) ABSTRACT

Methods of monitoring the expression of genes in malignant oral cells is disclosed. Gene expression profiles are used to identify markers associated with malignant oral cells and to diagnose oral cancer.

19 Claims, 21 Drawing Sheets

OTHER PUBLICATIONS

Ohyama et al., "Laser Capture Microdissection-Generated Target Sample for High-Density Oligonucleotide Array Hybridization," *Biotechniques*, 29(3):530-536 (2000).

Palazzolo et al., "Phage lambda cDNA cloning vectors for subtractive hybridization, fusion-protein synthesis and Creo-*loxP* automatic plasmid subcloning," *Gene*, 88:25-36 (1990).

Park et al., "*CYP1AI* and *GSTM1* Polymorphisms and Oral Cancer Risk," *Cancer Epidemiol. Biomarkers Prev.*, 6:791-797 (1997).

Perou et al., "Molecular portraits of human breast tumors," *Nature*, 406:747-752 (2000).

Redfern et al., "Conditional expression of a $G_i$-coupled receptor causes ventricular conduction delay and a lethal cardiomyopathy," *Proc. Nat'l. Acad. Sci. U.S.A.*, 97:4826-4831 (2000).

Sato et al., "Genetic polymorphism of drug-metabolizing enzymes and susceptibility to oral cancer," *Carcinogenesis*, 20:1927-1931 (1999).

Sgroi et al., "*In Vivo* Gene Expression Profile Analysis of Human Breast Cancer Progression," *Cancer Res.*, 59:5656-5661 (1999).

Shillitoe et al., "Genome-wide analysis of oral cancer—early results from the Cancer Genome Anatomy Project," *Oral Oncol.*, 36:8-16 (2000).

Tamayo et al., "Interpreting patterns fo gene expression with self-organizing maps: Methods and application to hemotopoeitic differentiation," *Proc. Natl. Acad. Sci. U.S.A.*, 96:2907-2912 (1999).

Warrington et al., "Large-Scale Genomic Analysis Using Affymetrix GeneChip® Probe Arrays," *Microarray Biochip Technology*, 6:119-148 (2000).

Weinberg, "Tumor Suppressor Genes," *Science* 254:1138-1146 (1991).

Wodicka et al., "Genome-wide expression monitoring in *Saccharomyces cerevisiae*," *Nat'l. Biotechnol.*, 15:1359-1367 (1997).

Wu and Wallace, "The Ligation Amplification Reaction (LAR)—Amplification of Specific DNA Sequences Using Sequential Rounds of Template-Dependent Ligation," *Genomics*, 4:560-569 (1989).

Zhang et al., "Gene Expression Profiles in Normal and Cancer Cells," *Science*, 276:1268-1272 (1997).

Janot et al., "Principal xenobiotic-metabolizing enzyme systems in human head and neck squamos cell carcinoma," *Carcinogensis*, 14:1279-1283 (1993).

Junien et al., "Direct Gene Dosage Determination in Patients with Unbalanced Chromosomal Abberation using Cloned DNA Sequences . . . ," *Am. J. Hum. Genet.*, 35:584-591 (1983).

Kawamata et al., "Possible Contribution of Active MMP2 to Lymph-Node Metastasis and Secreted Cathepsin L to Bone Invasion of newly Established Human Oral-Squamous-Cancer Cell Lines," *Int. J. Cancer*, 70:120-127 (1997).

Kimura et al., "Conventional tumor markers are prognostic indicators in patients with head and neck squamous cell carcinoma," *Cancer Lett.*, 155:163-168 (2000).

Kurokawa et al., "Manganese Superoxide Dismutase (Mn-SOD) Correlates with Prognosis of Patients with Oral Squamous Cell Carcinoma," *Fukuoka Igaku Zasshi*, 39:321-327 (1998).

Lin and Chen, "Creating kinase isoenzymes activity in serum and buccal pouch tissue of hamsters during DMBA-induced squamos cell carcinogenesis," *J. Oral Pathol. Med.*, 20;479-485 (1991).

Liu et al., "Circulating Intercellular adhesion molecule 1 (ICAM-1), E-selectin and vascular cell adhesion molecule 1 (VCAM-1) in head and neck cancer," *Br. J. Cancer*, 79:360-362 (1999).

Lotan et al., "Roles of Retinoids and their Nuclear Receptors in the Development and Prevention of Upper Aerodigestive Tract Cancers," *Environ. Health Perspect.*, 150(Suppl. 4):985-988 (1997).

Loukinova et al., "Growth Regulated Oncogene-α expression by murine squamous cell carcinoma promotes tumor growth, metastasis, leukocyte infiltration and angiogenesis by a host CXC Receptor-2 dependent mechanism," *Oncogene*, 19:3477-3486 (2000).

Magary et al., "Expression of matrix metalloproteinases and tissue inhibitor of metalloproteinases in laryngeal and pharyngeal squamous cell carcinoma: A quantitative analysis," *Otolaryngol Head Neck Surg.*, 122:712-716 (2000).

Mighell et al., "RT-PCR Investigation of Fibronectin mRNA Isoforms in Malignant, Normal and Reactive Oral Mucosa," *Oral Oncol.*, 33:155-162 (1997).

Muramatsu et al., "Superoxide Dismutase in SAS Human Tongue Carcinoma Cell Line is a Factor Defining Invasiveness and Cell Motility," *Cancer Res.*, 55:6210-6214 (1995).

Murray et al.; "Cytochrome P450 expression in oesophageal cancer," *Gut*, 35:599-603 (1994).

Ondrey et al., "Constitutive Activation of Transcription Factors NF-$_L$B, AP-1, and NF-IL6 in Human Head and Neck Squamous Cell Carcinoma Cell Lines that Express Pro-inflammatory and Pro-angiogenic Cytokines," *Mol. Carcinog.*, 26:119-129 (1999).

Porte et al., "Overexpression of Stromelysin-3, BM-40/SPARC, and MET Genes in Human Esophageal Carcinoma: Implications of Prognosis," *Clin. Cancer Res.*, 4:1375-1382 (1998).

Shin et al., "Biomarkers in Upper Aerodigestive Tract Tumorigensis: A Review," *Cancer Epidem., Biomarkers & Prev.*, 3:697-709 (1994).

Shintani et al., "Prognostic significance of ERRB3 overexpression in oral squamous cell carcinoma," *Cancer Lett.*, 95:79-83 (1995).

Strojan et al., "Prognostic Significance of Cysteine Proteinases Cathespins B and L and their Endogenous Inhibitors Stefins A and B in Patients with Squamos Cell Carcinoma of the Head and Neck," *Clin. Cancer Res.*, 6:1052-1062 (2000).

Suo et al., "Squamos cell carcinomas . . . ," *Histopathology*, 23:45-54 (1993).

Viaene and Baert, "Expression of Cytokeratin-mRNAs in squamous-cell carcinoma and balloon-cell formation fo human oesophageal epithelium," *Histochem. J.*, 27:69-78 (1995).

von Biberstein et al., "Interleukin-1 Receptor Antagonist in Head and Neck Squamous Cell Carcinoma," *Arch. Otolaryngol. Head Neck Surg.*, 122:751-759 (1996).

Yeudall et al., "Functional Characterization of p53 Molecules Expressed in Human Squamos Cell Carcinomas of the Head and Neck," *Mol. Carcinog.*, 18:89-96 (1997).

* cited by examiner

Figure 1A    LCM, RNA isolation and amount of cDNA after 2 rounds of T7 amplification

|  | Case 1 | | Case 2 | | Case 3 | | Case 4 | | Case 5 | |
| --- | --- | --- | --- | --- | --- | --- | --- | --- | --- | --- |
|  | Normal | Cancer | Normal | Cancer | Normal | Cancer | Normal | Cancer | Normal | Cancer |
| Number of LCM shots | 48,000 | 40,000 | 40,000 | 40,000 | 40,000 | 40,000 | 40,000 | 40,000 | 40,000 | 40,000 |
| Approx # of cells | 200,000 | 120,000 | 120,000 | 120,000 | 120,000 | 120,000 | 120,000 | 120,000 | 120,000 | 120,000 |
| Approx amt of RNA used for T7 amp | 100ng | 75ng | 100ng | 120ng | 100ng | 115ng | 100ng | 100ng | 100ng | 100ng |
| ds-cDNA amt after 2 rounds of T7 amp | 8.75µg | 5.88µg | 1.56µg | 6.88µg | 2.5µg | 2.97µg | 23.5µg | 6.0µg | 17.74µg | 23.13µg |

Amount of ds-cDNA after 2 rounds of T7 amplification is dependent on the quality of the LCM-generated RNA from the normal and tumor tissues Figure 1B    Percent transcripts detected in normal and tumor tissues

|  | Case 1 | | Case 2 | | Case 3 | | Case 4 | | Case 5 | |
| --- | --- | --- | --- | --- | --- | --- | --- | --- | --- | --- |
|  | Normal | Cancer | Normal | Cancer | Normal | Cancer | Normal | Cancer | Normal | Cancer |
| % Genes detected | 25.8 | 30.3 | 30.3 | 33.0 | 29.4 | 30.3 | 35.3 | 35.8 | 40.3 | 40.2 |

Figure 2A: 39 Genes whose expression changed in 5/5 cases

| Accession Number | Name | Chromosome Localization | Oral Cancer Association | References |
|---|---|---|---|---|
| Increase in Tumor | | | | |
| D86983 | p53-responsive gene 2 | 2pter-p25.1 | Yes | (Yeudall et al., 1997) |
| J03040 | Secreted protein, acidic, cysteine-rich, osteonectin | 5q31.3-q32 | Yes | (Porte et al., 1998) |
| M11147 | Ferritin, light polypeptide | 19q13.3-q13.4 | Yes | (Kimura et al., 2000) |
| X12451 | Cathepsin L | 9q21-q22 | Yes | (Kawamata et al., 1997; Strojan et al., 2000) |
| X17042 | Proteoglycan 1, secretory granule | 10q22.1 | | |
| X54925 | Matrix metalloproteinase 1 (interstitial collagenase) | 11q22.3 | Yes | (Magary et al., 2000) |
| Z29083 | 5T4 oncofetal trophoblast glycoprotein | 6 | | |
| D43968 | Runt-related transcription factor 1 (acute myeloid leukemia 1) | 21q22.23 | | |
| X02761 | Fibronectin 1 | 2q34 | Yes | (Mighell et al., 1997) |
| Z74616 | Collagen, type I, alpha 2 | 7q22.1 | | |
| X57579 | Inhibin, beta A (activin A, activin AB alpha polypeptide) | 7p15-p13 | | |
| M30257 | Vascular cell adhesion molecule 1 | 1p32-p31 | Yes | (Liu et al., 1999) |
| M55998 | Human alpha-1 collagen type I gene, | N/A | | |
| X65965 | Superoxide dismutase 2, mitochondrial | 6q25.3 | Yes | (Kurokawa et al., 1998; Muramatsu et al., 1995) |
| X54489 | GRO1 oncogene (melanoma growth stimulating activity, alpha) | 4q21 | Yes | (Loukinova et al., 2000) |
| L13923 | Fibrillin 1 (Marfan Syndrome) | 15q21.1 | | |
| | Name | | | |
| Decrease in Tumor | | | | |
| X78932 | Zinc finger protein 273 | N/A | | |
| J04469 | Creatine kinase, mitochondrial 1 (ubiquitous) | 15q15 | Yes | (Lin & Chen, 1991) |
| L05779 | Epoxide hydrolase 2, cytoplasmic | 8p21-p12 | Yes | (Janot et al., 1993) |
| M32402 | Placental protein 11 (serine proteinase) | 12q13.1 | | |
| M69177 | Monoamine oxidase B | Xp11.4-p11.3 | | |

Figure 2A Continued: 39 Genes whose expression changed in 5/5 cases

| Accession | Name | Location | | Reference |
|---|---|---|---|---|
| M98447 | Transglutaminase 1 (K polypeptide epidermal type I, protein-glutamine-gamma-glutamyltransferase) | 14q11.2 | Yes | (Shin et al., 1994) |
| U17077 | BENE protein | 2q13 | | |
| U34252 | Aldehyde dehydrogenase 9 (gamma-aminobutyraldehyde dehydrogenase, E3 isozyme) | 1q22-q23 | | |

| | Name | | | |
|---|---|---|---|---|
| Decrease in Tumor (Cont) | | | | |
| U46689 | Aldehyde dehydrogenase 10 (fatty aldehyde dehydrogenase) | 17p11.2 | | |
| U67963 | Lysophospholipase-like | 3 | | |
| U83115 | Absent in melanoma 1 | 6q21 | | |
| U90902 | Human clone 23612 | N/A | | |
| X07695 | Keratin 4 | 12q13 | Yes | (Suo et al., 1993) |
| X07696 | Keratin 15 | 17q21 | Yes | (Viaene & Baert, 1995) |
| X76029 | Neuromedin U | 4q12 | | |
| X76180 | Sodium channel, nonvoltage-gated 1 alpha | 12p13 | | |
| X78549 | Protein tyrosine kinase 6 | 20q13.3 | | |
| Y09267 | Flavin containing monooxygenase 2 | 1q23-q251 | | |
| Y09616 | Carboxylesterase 2 (intestine, liver) | 16 | | |
| Y07909 | Epithelial membrane protein 1 | 12p12.3 | | |
| X53296 | Interleukin 1 receptor antagonist | 2q14.2 | Yes | (von Biberstein et al., 1996) |
| M61855 | Cytochrome P450, subfamily IIC (mephenytoin4-hydroxylase), polypeptide 9 | 10q24 | Yes | (Murray et al., 1994) |
| U18934 | TYRO3 protein tyrosine kinase | 15q15.1-q21.1 | | |

Figure 2B: Representative sample of differentially regulated genes

| Accession Number | Description/Function | Chromosomal Location | Altered Regulation |
|---|---|---|---|
| Metastatic/Invasion Pathway | | | |
| X12451 | Cathepsin-L | 9q21-22 | Up 5/5 |
| X54925 | Collagenase/MMP I | 11q22.3 | Up 5/5 |
| X02419 | UPA | 10q24 | Up 5/5 |
| Z29083 | 5T4 Oncofetal protein | 6q13-14 | Up 5/5 |
| Transcriptional factors | | | |
| D43968 | Runt-related transcription factor/AML1 | 21q22 | Up 5/5 |
| U85658 | ERF1 transcription factor | 20q13.2 | Down 4/5 |
| Onco-genes/suppressors | | | |
| M57731 | Gro-Beta Oncogene | 4q12-13 | Up 4/5 |
| M16038 | Lyn-tyrosine kinase (oncogene LYN) | 8q13 | Up 4/5 |
| L13698 | Gas-1 | 9q21.3-22.1 | Up 4/5 |
| Y07909 | Tumour associated membrane protein (control cell-Cekk interactions & cell proliferation) | 12p12.3 | Down 5/5 |
| X98311 | CEA2 (onco-suppressor) | 19q13.2 | Down 5/5 |
| M16750 | PIM-1-oncogene | 6p21.2 | Down 4/5 |
| U83115 | AIM1 (onco-suppressor) | 6q21 | Down 4/5 |
| Differentiation Markers | | | |
| X07695 | Cytokeratin 4 | 12q13 | Down 5/5 |
| X07696 | Cytokeratin 15 | 17q21 | Down 5/5 |
| M98447 | Transglutaminase 1 | 14q11.2 | Down 5/5 |
| Others | | | |
| U37546 | Apoptosis-inhibitor protein | 11q22-23 | Up 5/5 |
| X76029 | Neuromedin U | 4q12 | Down 5/5 |
| S45630 | Alpha-beta-crystallin/Rosenthal protein | 11q22.3-23.1 | Down 4/5 |
| X78932 | ZFP_HZF9 (potent repressor) | 19p12 | Down 5/5 |
| U47414 | Cyclin G2 (cell cycle regulators) | 4q21 | Down 4/5 |

Figure 2C    UP REGULATED GENES

| Probe set | Description | Ave FC | Method* | T-test |
|---|---|---|---|---|
| X54925 | MMP1, type I interstitial collagenase | 429 | G | 0.093 |
| X05232 | MMP3, stromelysin-1 | 177 | G | 0.047 |
| X57579 | Activin β-A subunit | 146 | G | 0.066 |
| U24577 | LDL-phospholipase A2 | 133 | G | 0.003 |
| X54489 | Melanoma growth stimulatory activity | 93 | G M Gc | 0.040 |
| L23808 | MMP12 | 70 | G | 0.060 |
| X04602 | Interleukin BSF-2 | 59 | G | 0.256 |
| U20758 | Osteopontin, SPP1 | 47 | G | 0.224 |
| M21121 | T cell-specific protein, RANTES | 40 | G | 0.129 |
| U09278 | Fibroblast activation protein | 39 | G | 0.087 |
| X51441 | Serum amyloid A, SAA | 39 | G | 0.037 |
| M63438 | Immunoglobulin kappa variable 1D-8 | 35 | G | 0.071 |
| Z19574 | Cytokeratin 17 | 34 | G | 0.125 |
| Z49194 | Oct-binding factor | 28 | G Gc | 0.081 |
| U28488 | Complement component 3a receptor 1 | 25 | G | 0.006 |
| V00536 | IFN-γ | 24 | G | 0.150 |
| X02761 | Fibronectin | 21 | G | 0.115 |
| J03040 | Osteonectin / SPARC | 20 | Gc | 0.227 |
| D55696 | Cysteine protease | 19 | Gc | 0.022 |
| X52022 | Collagen, type VI α3 | 18 | G | 0.202 |
| U89942 | Lysyl oxidase-related protein | 18 | Gc G | 0.082 |
| M12759 | Ig J chain | 18 | G | 0.218 |
| L13286 | 1,25-dihydroxyvitamin D3 24-hydroxylase | 17 | Gc G | 0.052 |
| X66867 | Max | 16 | Gc | 0.304 |
| J05070 | MMP9, type IV collagenase | 16 | G | 0.287 |
| M87789 | IGHG3, Ig heavy constant γ 3 | 16 | G | 0.102 |
| X54867 | NKG2, lectin-like receptor subfamily C | 14 | G | 0.171 |
| M13755 | Interferon induced 17KDa/15KDa | 13 | G | 0.052 |

*G=GeneChip, M=Matlab, Gc=GeneCluster

Figure 2D   DOWN REGULATED GENES

| Probe set | Description | Ave FC | Method* | T-test |
|---|---|---|---|---|
| X51420 | Tyrosinase-related protein | 0.06 | M | 0.202 |
| X07695 | Cytokeratin 4C | 0.06 | G M | 0.002 |
| U09578 | MAPKAP kinase | 0.08 | M | 0.238 |
| Z84721 | Globin, α and ζ | 0.08 | M | 0.036 |
| M32402 | Placental protein, PP11 | 0.10 | G M | 0.005 |
| HG3884-HT4154 | Homeotic Protein, Hpx-42 | 0.10 | G | 0.006 |
| U85707 | Leukemogenic homolog protein, MEIS1 | 0.10 | G M | 0.008 |
| X76180 | Ung amiloride sensitive Na+ channel protein | 0.10 | G M | 0.011 |
| Y09267 | Flavin-containing monooxygenase 2 | 0.10 | M | 0.036 |
| X95240 | Cysteine-rich secretory protein 3 | 0.10 | M | 0.141 |
| X07696 | Cytokeratin 15 | 0.11 | G M | 0.004 |
| X76223 | MAL, t cell differentiation protein | 0.11 | G M | 0.041 |
| U49114 | Prohormone convertase 5 precursor, PC5 | 0.14 | M | 0.102 |
| D13643 | KIAA0018 | 0.14 | Gc | 0.001 |
| U65932 | Extracellular matrix protein 1, ECM1 | 0.14 | M | 0.048 |
| M25079 | Sickle cell β-globin | 0.14 | M | 0.085 |
| M83186 | Cytochrome c oxidase subunit VIIa | 0.14 | M | 0.036 |
| D00408 | Cytochrome P-450, fetal liver | 0.14 | G M Gc | 0.022 |
| M27160 | Tyrosinase, TYR | 0.15 | M | 0.085 |
| X87159 | Epithelial amiloride-sensitive Na+ channel, β | 0.15 | G | 0.003 |
| Y07909 | Progression Associated Protein | 0.15 | M | 0.004 |
| X76029 | Neuromedin U | 0.15 | G M Gc | 0.000 |
| D29958 | KIAA0116 | 0.15 | Gc | 0.050 |
| U06643 | Keratinocyte lectin 14, HKL-14 | 0.15 | M Gc | 0.001 |
| X53296 | IRAP | 0.16 | G M | 0.012 |
| U15932 | Protein phosphatase | 0.16 | M | 0.045 |
| HG4236-HT4506 | Zinc Finger Protein, Znf138 | 0.16 | G | 0.079 |
| D80010 | KIAA0188 | 0.17 | M | 0.000 |

* G = GeneChip, M = Matlab, Gc = GeneCluster

Figure 3  Comparison of percent increases for 3 upregulated genes measured by GeneChip and Real-Time Quantitative PCR Data*

| | Samples | 1 | 2 | 3 | 4 | 5 |
|---|---|---|---|---|---|---|
| Accession | Gene | GC/RTQPCR | GC/RTQPCR | GC/RTQPCR | GC/RTQPCR | GC/RTQPCR |
| X54925 | Collagenase | 4300 / 1100 | 22900 / 36800 | 800 / 5500 | 49500 / 130000 | 7800 / 16500 |
| X12451 | Pro-cathepsin L | 300 / 800 | 570 / 700 | 180 / 300 | 300 / 2800 | 300 / 400 |
| X02419 | UPA | 400 / 100 | 440 / 800 | 150 / 3200 | 400 / 980 | 425 / 900 |

GC= Gene expression data
RT-QPCR= real time quantitative PCR

Figure 6: Differentially Expressed Genes Identified by All 3 Methods

| Accession Number | Name | Expression Up/Down in Oral Cancer | Chromosome Localization | Oral Cancer Association | References |
|---|---|---|---|---|---|
| D00408 | Cytochrome P450, subfamily IIIA polypeptide 7 | See Comment 1 | ND | | |
| D13666 | Osteoblast specific factor 2 | Up in Cancer | 13 | | |
| D42047 | KIAA0089 | Down in Cancer | 3 | | |
| D43968 | Runt-related transcription factor 1 | Up in Cancer | 21q22.3 | | |
| D84276 | CD38 antigen (p45) | Up in Cancer | 4p15 | | |
| HG3494-HT3688 | Nuclear Protein IL6 | Up in Cancer | ND | Yes | (Ondrey et al., 1999) |
| J03258 | Vitamin D receptor | Down in Cancer | 12q12-q14 | Yes | (Lotan, 1997) |
| J03473 | ADP-ribosyltransferase | Up in Cancer | 1q41-q42 | | |
| J03909 | Interferon, gamma inducible protein 30 | Up in Cancer | 19p13.1 | | |
| J04080 | Complement component 1, s subcomponent | Up in Cancer | 12p13 | | |
| M14200 | Diazepam binding inhibitor | Down in Cancer | 2q12-q21 | | |
| M15661 | Ribosomal protein L36a | Down in Cancer | 14 | | |
| M34309 | v-erb-b2 avian erythroblastic leukemia viral oncogene homolog3 | Down in Cancer | 12q13 | Yes | (Shintani et al., 1995) |
| M69177 | Monoamine oxidase B | Down in Cancer | Xp11.4-p11.3 | | |
| M81182 | ATP-binding cassette, subfamily D | Down in Cancer | 1p22-p21 | | |
| S45630 | Crystallin, alpha B | Down in Cancer | 11q22.3-q23.1 | | |
| U18934 | TYRO3 protein tyrosine kinase | Down in Cancer | 15q15.1-q21.1 | | |
| U34252 | Aldehyde dehydrogenase 9 | Down in Cancer | 1q22-q23 | | |
| U46689 | Aldehyde dehydrogenase 10 | Down in Cancer | 17p11.2 | | |
| U56814 | Deoxyribonuclease I-like 3 | Down in Cancer | 3p21.1-p14.3 | | |
| X12451 | Cathepsin L | Up in Cancer | 9q21-q22 | Yes | (Kawamata et al., 1997; Strojan et al., 2000) |
| X54489 | GRO1 oncogene (MGSA) | Up in Cancer | 4q21 | Yes | (Loukinova et al., 2000) |
| X76029 | Neuromedin U | Down in Cancer | 4q12 | | |
| X78932 | Zinc finger protein 273 | Down in Cancer | ND | | |
| X87241 | FAT tumor suppressor | Up in Cancer | 4q34-q35 | | |
| Y00815 | Protein tyrosine phosphatase, receptor, type, F | Down in Cancer | 1q34 | Yes | |
| Z29083 | 5T4 oncofetal trophoblast glycoprotein | Up in Cancer | 6 | | |

FIGURE 7A

| Probe Set | Description |
|---|---|
| AB000114_at | "AB000114, class A, 20 probes, 20 in AB000114 1818-2208, Human mRNA for osteomodulin, complete cds" |
| AB000115_at | "AB000115, class A, 20 probes, 20 in AB000115 1469-1973, Human mRNA, complete cds" |
| AC002115_cds1_at | "AC002115, class A, 20 probes, 16 in AC002115mRNA#2 3349-7559: 4 not in GB record, COX6B gene (COXG) extracted from Human DNA from overlapping chromosome 19 cosmids R31396, F25451, and R31076 containing COX6B and UPKA, genomic sequence, COX6B gene (COXG) e" |
| AF008445_at | "AF008445, class A, 20 probes, 20 in AF008445 895-1387, Homo sapiens phospholipid scramblase mRNA, complete cds. /gb=AF008445 /ntype=RNA" |
| D00003_s_at | "D00003, class B, 12 probes, 12 in D00003 1681-1981, Human liver cytochrome P-450 mRNA, complete cds, Human liver cytochrome P-450 mRNA, complete cds" |
| D00408_s_at | "D00408, class B, 11 probes, 11 in D00408 1373-1921, Human fetal liver cytochrome P-450 (P-450 HFLa), complete cds, Human fetal liver cytochrome P-450 (P-450 HFLa), complete cds" |
| D11151_at | "D11151, class A, 20 probes, 20 in D11151exon 1936-2434, Human DNA for endothelin-A receptor, 5' flanking region and" |
| D12775_s_at | "D12775, class A, 20 probes, 20 in D12775 3124-3662, Human mRNA for erythrocyte-specific AMP deaminase, complete cds" |
| D13644_at | "D13644, class A, 20 probes, 20 in D13644 4013-4523, Human mRNA for KIAA0019 gene, complete cds" |
| D13666_s_at | "D13666, class A, 20 probes, 20 in D13666 2630-3072, Homo sapiens mRNA for osteoblast specific factor 2 (OSF-2os)" |
| D14520_at | "D14520, class A, 20 probes, 20 in D14520 718-1258, Human mRNA for GC-Box binding protein BTEB2, complete cds" |
| D14658_at | "D14658, class A, 20 probes, 20 in D14658 859-1285, Human mRNA for KIAA0102 gene, complete cds" |
| D16217_at | "D16217, class A, 20 probes, 20 in D16217 1904-2414, Human mRNA for calpastatin, complete cds" |
| D21255_at | "D21255, class A, 20 probes, 20 in D21255 3362-3812, Human mRNA for OB-cadherin-2, complete cds" |
| D25304_at | "D25304, class A, 20 probes, 20 in D25304 4431-4701, Human mRNA for KIAA0006 gene, partial cds" |
| D28915_at | "D28915, class A, 20 probes, 16 in D28915cds 1002-1272: 4 in reverseSequence, 114-186, Human gene for hepatitis C-associated microtubular aggregate protein p44" |
| D31883_at | "D31883, class A, 20 probes, 20 in D31883 6153-6711, Human mRNA for KIAA0059 gene, complete cds" |
| D31887_at | "D31887, class A, 20 probes, 20 in D31887 4050-4512, Human mRNA for KIAA0062 gene, partial cds" |
| D32129_f_at | "D32129, class A, 20 probes, 20 in D32129 920-1425, Human mRNA for HLA class-I (HLA-A26) heavy chain, complete cds (clone cMIY-1)" |
| D38551_at | "D38551, class A, 20 probes, 20 in D38551 3082-3592, Human mRNA for KIAA0078 gene, complete cds" |
| D42047_at | "D42047, class A, 20 probes, 20 in D42047 3472-3970, Human mRNA for KIAA0089 gene, partial cds" |
| D42073_at | "D42073, class A, 20 probes, 20 in D42073 1551-2049, Human mRNA for reticulocalbin, complete cds" |
| D43636_at | "D43636, class A, 20 probes, 20 in D43636 3576-4080, Human mRNA for KIAA0096 gene, partial cds" |
| D43682_s_at | "D43682, class A, 20 probes, 20 in D43682 1584-2115, Human mRNA for very-long-chain acyl-CoA dehydrogenase (VLCAD), complete cds" |
| D43968_at | "D43968, class A, 20 probes, 20 in D43968 6790-7222, Human AML1 mRNA for AML1b protein (alternatively spliced product), complete cds" |
| D49387_at | "D49387, class A, 20 probes, 20 in D49387 401-917, Human mRNA for NADP dependent leukotriene b4 12-hydroxydehydrogenase, partial cds. /gb=D49387 /ntype=RNA" |
| D49489_at | "D49489, class A, 20 probes, 20 in D49489 1267-1759, Human mRNA for protein disulfide isomerase-related protein P5, complete cds" |
| D49950_at | "D49950, class A, 20 probes, 20 in D49950 495-918, Human Liver mRNA for interferon-gamma inducing factor(IGIF), complete cds" |
| D61391_at | "D61391, class A, 20 probes, 20 in D61391 1169-1685, Human mRNA for phosphoribosypyrophosphate synthetase-associated protein 39, complete cds" |
| D79987_at | "D79987, class A, 20 probes, 20 in D79987 6109-6523, Human mRNA for KIAA0165 gene, complete cds" |

FIGURE 7B

| | | |
|---|---|---|
| D79990_at | "D79990, class A, 20 probes, 20 in D79990 5065-5383, Human mRNA for KIAA0168 gene, complete cds" |
| D79992_at | "D79992, class A, 20 probes, 20 in D79992 6597-6897, Human mRNA for KIAA0170 gene, complete cds" |
| D79994_at | "D79994, class A, 20 probes, 20 in D79994 4227-4749, Human mRNA for KIAA0172 gene, partial cds" |
| D80000_at | "D80000, class A, 20 probes, 20 in D80000 5250-5754, Human mRNA for KIAA0178 gene, partial cds" |
| D80010_at | "D80010, class A, 20 probes, 20 in D80010 4778-5198, Human mRNA for KIAA0188 gene, partial cds" |
| D83018_at | "D83018, class A, 20 probes, 20 in D83018 2645-3149, Human mRNA for nel-related protein 2, complete cds" |
| D84239_at | "D84239, class A, 20 probes, 20 in D84239 15949-16339, Human mRNA for IgG Fc binding protein, complete cds" |
| D84276_at | "D84276, class A, 20 probes, 18 in D84276 909-1185: 2 in reverseSequence, 1299-1305, Human mRNA for CD38, complete cds" |
| D85181_at | "D85181, class A, 20 probes, 20 in D85181 1502-2018, Human mRNA for fungal sterol-C5-desaturase homolog, complete cds" |
| D85429_at | "D85429, class A, 20 probes, 20 in D85429exon#3 813-1347, Human DNA for heat shock protein 40, complete cds" |
| D86956_at | "D86956, class A, 20 probes, 20 in D86956 3139-3589, Human mRNA for KIAA0201 gene, complete cds" |
| D86957_at | "D86957, class A, 20 probes, 20 in D86957 3869-4265, Human mRNA for KIAA0202 gene, partial cds" |
| D86959_at | "D86959, class A, 20 probes, 20 in D86959 5435-5867, Human mRNA for KIAA0204 gene, complete cds" |
| D86961_at | "D86961, class A, 20 probes, 20 in D86961 3678-4188, Human mRNA for KIAA0206 gene, partial cds" |
| D86974_at | "D86974, class A, 20 probes, 20 in D86974 5077-5308, Human mRNA for KIAA0220 gene, partial cds" |
| D86983_at | "D86983, class A, 20 probes, 20 in D86983 5131-5485, Human mRNA for KIAA0230 gene, partial cds" |
| D86985_at | "D86985, class A, 20 probes, 20 in D86985 5502-5946, Human mRNA for KIAA0232 gene, complete cds" |
| D87119_at | "D87119, class A, 20 probes, 20 in D87119 3614-4160, Human cancellous bone osteoblast mRNA for GS3955, complete cds" |
| D87258_at | "D87258, class A, 20 probes, 20 in D87258 1489-1999, Human cancellous bone osteoblast mRNA for serin protease with IGF-binding motif, complete cds" |
| D87445_at | "D87445, class A, 20 probes, 20 in D87445 6334-6892, Human mRNA for KIAA0256 gene, complete cds" |
| HG1428-HT1428_s_at | "Globin, Beta" |
| HG1612-HT1612_at | Macmarcks |
| HG1686-HT4572_s_at | "Transcription Factor E4tf1, Respiratory, Gamma 2 Subunit, Alt. Splice 4" |
| HG2090-HT2152_s_at | "External Membrane Protein, 130 Kda" |
| HG2788-HT2896_at | Calcyclin |
| HG3431-HT3616_s_at | "Decorin, Alt. Splice 1" |
| HG3494-HT3688_at | Nuclear Factor Nf-Il6 |
| HG3570-HT3773_at | Protein Phosphatase Inhibitor Homolog |
| HG4297-HT4567_at | Transcriptional Coactivator Pc4 |
| HG4334-HT4604_s_at | Glycogenin |
| HG4557-HT4962_at | "Small Nuclear Ribonucleoprotein U1, 1snrp" |
| HG658-HT658_f_at | "Major Histocompatibility Complex, Class I, C" |
| J00277_at | "J00277, class C, 20 probes, 20 in all_J00277 3607-3724, Human (genomic clones lambda-[SK2-T2, HS578T]; cDNA clones RS-[3,4, 6]) c-Ha-ras1 proto-oncogene, complete coding sequence" |
| J02871_s_at | "J02871, class A, 20 probes, 20 in J02871 1475-1931, Human lung cytochrome P450 (IV subfamily) BI protein, complete cds" |
| J03040_at | "J03040, class A, 20 probes, 20 in J03040 1508-2000, Human SPARC/osteonectin mRNA, complete cds" |
| J03077_s_at | "J03077, class A, 20 probes, 20 in J03077 2159-2692, Human co-beta glucosidase (proactivator) mRNA, complete cds" |
| J03258_at | "J03258, class A, 20 probes, 20 in J03258mRNA 4003-4561, Human vitamin D receptor mRNA, complete cds" |
| J03473_at | "J03473, class A, 20 probes, 20 in J03473mRNA 3212-3752, Human poly(ADP-ribose) synthetase mRNA, complete cds" |
| J03474_at | "J03474, class A, 20 probes, 20 in J03474cds 3-255, Human serum amyloid A gene, complete cds" |
| J03827_at | "J03827, class A, 20 probes, 20 in J03827 970-1438, Y box binding protein-1 (YB-1) mRNA" |
| J03909_at | "J03909, class A, 20 probes, 20 in J03909 461-995, Human gamma-interferon-inducible protein (IP-30) mRNA, complete cds" |

FIGURE 7C

| Probe ID | Description |
|---|---|
| J04056_at | "J04056, class A, 20 probes, 20 in J04056 746-1118, Human carbonyl reductase mRNA, complete cds" |
| J04076_at | "J04076, class A, 20 probes, 20 in J04076mRNA 2171-2651, Human early growth response 2 protein (EGR2) mRNA, complete cds" |
| J04080_at | "J04080, class A, 20 probes, 20 in J04080mRNA 2136-2604, Human complement component C1r mRNA, complete cds" |
| J04093_s_at | "J04093, class A, 20 probes, 20 in J04093 1842-2342, Homo sapiens phenol UDP-glucuronosyltransferase (UDPGT) mRNA, complete cds" |
| J04130_s_at | "J04130, class A, 20 probes, 20 in J04130mRNA 87-634, Human activation (Act-2) mRNA, complete cds" |
| J04162_at | "J04162, class A, 20 probes, 20 in J04162mRNA 1406-1940, Human leukocyte IgG receptor (Fc-gamma-R) mRNA, complete cds" |
| J04164_at | "J04164, class A, 20 probes, 20 in J04164 366-804, Human interferon-inducible protein 27-Sep mRNA, complete cds" |
| J04177_at | "J04177, class A, 20 probes, 20 in J04177 5773-6133, Human alpha-1 type XI collagen (COL11A1) mRNA, complete cds" |
| J04469_at | "J04469, class B, 20 probes, 11 in J04469exon#9 11-173: 9 not in GB record, Human mitochondrial creatine kinase (CKMT) gene, complete cds" |
| J05070_at | "J05070, class A, 20 probes, 20 in J05070 1805-2303, Human type IV collagenase mRNA, complete cds" |
| J05633_at | "J05633, class A, 20 probes, 20 in J05633 2714-3008, Human integrin beta-5 subunit mRNA, complete cds" |
| K03430_at | "K03430, class C, 20 probes, 20 in all K03430 414-853, Human complement C1q B-chain gene" |
| L00352_at | "L00352, class A, 20 probes, 20 in L00352exon 1952-2492, Human low density lipoprotein receptor gene" |
| L05187_at | "L05187, class C, 20 probes, 20 in all L05187 2284-2339, Homo sapiens small proline-rich protein 1 (SPRR1A) gene, complete cds" |
| L05779_at | "L05779, class A, 20 probes, 20 in L05779 1535-2069, Human cytosolic epoxide hydrolase mRNA, complete cds" |
| L06797_s_at | "L06797, class A, 20 probes, 20 in L06797 1041-1599, Human (clone L5) orphan G protein-coupled receptor mRNA, complete cds" |
| L06895_at | "L06895, class A, 20 probes, 20 in L06895 503-977, Homo sapiens antagonizer of myc transcriptional activity (Mad) mRNA, complete cds" |
| L08895_at | "L08895, class C, 20 probes, 20 in all L08895 3518-4059, Homo sapiens MADS/MEF2-family transcription factor (MEF2C) mRNA, complete cds" |
| L10373_at | "L10373, class A, 20 probes, 20 in L10373 1311-1713, Human (clone CCG-B7) mRNA sequence" |
| L10386_at | "L10386, class A, 20 probes, 20 in L10386 2036-2498, Homo sapiens transglutaminase E3 (TGASE3) mRNA, complete cds" |
| L10678_at | "L10678, class A, 20 probes, 20 in L10678 1128-1650, Human profilin II mRNA, complete cds" |
| L10717_at | "L10717, class A, 20 probes, 20 in L10717 6303-6332, Homo sapiens T cell-specific tyrosine kinase mRNA, complete cds" |
| L11370_at | "L11370, class A, 20 probes, 20 in L11370 3486-4038, Human protocadherin 42 mRNA, complete cds for abbreviated PC42" |
| L11931_at | "L11931, class A, 20 probes, 20 in L11931 1454-1644, Human cytosolic serine hydroxymethyltransferase (SHMT) mRNA, complete cds" |
| L12350_at | "L12350, class A, 20 probes, 20 in L12350mRNA 5247-5721, Human thrombospondin 2 (THBS2) mRNA, complete cds" |
| L13286_at | "L13286, class A, 20 probes, 20 in L13286 2671-3205, Human mitochondrial 1,25-dihydroxyvitamin D3 24-hydroxylase mRNA, complete cds" |
| L13329_at | "L13329, class A, 20 probes, 20 in L13329exon 434-938, Homo sapiens iduronate-2-sulfatase (IDS) gene" |
| L13391_at | "L13391, class A, 20 probes, 20 in L13391exon#5 265-808, Human helix-loop-helix basic phosphoprotein (G0S8) gene, complete cds" |
| L13923_at | "L13923, class A, 20 probes, 20 in L13923 9109-9601, Homo sapiens fibrillin mRNA, complete cds" |
| L14837_at | "L14837, class A, 20 probes, 20 in L14837 7335-7839, Human tight junction (zonula occludens) protein ZO-1 mRNA, complete cds" |
| L19437_at | "L19437, class A, 20 probes, 20 in L19437 857-1211, Human transaldolase mRNA containing transposable element, complete cds" |
| L19605_at | "L19605, class A, 20 probes, 20 in L19605 1483-1915, Homo sapiens 56K autoantigen annexin XI gene mRNA, complete cds" |
| L19872_at | "L19872, class A, 20 probes, 20 in L19872 4756-5059, Human AH-receptor mRNA, complete cds" |
| L20591_at | "L20591, class B, 20 probes, 11 in L20591exon 1-295: 9 not in GB record, Human annexin III (ANX3) gene, alternative" |
| L23116_at | "L23116, class A, 20 probes, 20 in L23116 3296-3644, Homo sapiens galactocerebrosidase (GALC) mRNA, complete cds" |
| L23808_at | "L23808, class A, 20 probes, 20 in L23808 1297-1717, Human metalloproteinase (HME) mRNA, complete cds" |
| L24203_at | "L24203, class A, 20 probes, 20 in L24203 2423-2891, Homo sapiens ataxia-telangiectasia group D-associated protein mRNA, complete cds" |
| L27560_at | "L27560, class A, 20 probes, 20 in L27560mRNA 986-1262, Human insulin-like growth factor binding protein 5 (IGFBP5) mRNA" |
| L32179_at | "L32179, class A, 20 probes, 20 in L32179mRNA 1028-1556, Human arylacetamide deacetylase mRNA, complete cds" |
| L33842_mal_at | "L33842, class A, 20 probes, 20 in L33842mRNA 1213-1639, Homo sapiens (clone FFE-7) type II inosine monophosphate dehydrogenase (IMPDH2) gene, exons 1-13, complete cds" |
| L33930_s_at | "L33930, class A, 20 probes, 20 in L33930 1504-2054, Homo sapiens CD24 signal transducer mRNA, complete cds and 3' region" |

FIGURE 7D

| | |
|---|---|
| L34657_at | "L34657, class A, 20 probes, 20 in L34657mRNA 2757-3219, Homo sapiens platelet/endothelial cell adhesion molecule-1 (PECAM-1) gene" |
| L76465_at | "L76465, class A, 20 probes, 20 in L76465 1929-2493, Homo sapiens NAD+-dependent 15 hydroxyprostaglandin dehydrogenase (PGDH) mRNA, complete cds" |
| L77886_at | "L77886, class A, 20 probes, 20 in L77886 5390-5696, Human protein tyrosine phosphatase mRNA, complete cds" |
| M11147_at | "M11147, class A, 20 probes, 20 in M11147mRNA 251-689, Human ferritin L chain mRNA, complete cds" |
| M11718_at | "M11718, class A, 20 probes, 20 in M11718 716-1274, Human alpha-2 type V collagen gene, 3' end" |
| M12759_at | "M12759, class B, 20 probes, 12 in M12759cds 65-335: 8 in reverseSequence, 1020-1260, Human Ig J chain gene" |
| M13755_at | "M13755, class A, 20 probes, 20 in M13755mRNA 33-591, Human interferon-induced 17-kDa/15-kDa protein mRNA, complete cds" |
| M14199_s_at | "M14199, class A, 20 probes, 20 in M14199 2-381, Human laminin receptor (2H5 epitope) mRNA, 5' end" |
| M14200_ma1_at | "M14200, class A, 20 probes, 20 in M14200mRNA 139-469, Human diazepam binding inhibitor (DBI) mRNA, complete cds" |
| M14338_at | "M14338, class C, 20 probes, 20 in all_M14338 2740-3281, Human mRNA for protein S and intron" |
| M15661_at | "M15661, class A, 20 probes, 20 in M15661mRNA 3-338, Human ribosomal protein mRNA, complete cds" |
| M15841_at | "M15841, class A, 20 probes, 20 in M15841 492-945, Human U2 small nuclear RNA-associated B'' antigen mRNA, complete cds" |
| M16038_at | "M16038, class A, 20 probes, 20 in M16038 1817-2255, Human lyn mRNA encoding a tyrosine kinase" |
| M16750_s_at | "M16750, class A, 20 probes, 20 in M16750 1699-2210, Human pim-1 oncogene mRNA, complete cds" |
| M17183_s_at | "M17183, class C, 20 probes, 20 in all_M17183 531-752, Human parathyroid hormone-related protein mRNA, complete cds" |
| M18728_at | "M18728, class A, 20 probes, 20 in M18728mRNA 1932-2460, Human nonspecific crossreacting antigen mRNA, complete cds" |
| M18737_ma1_at | "M18737, class A, 20 probes, 20 in M18737mRNA 269-815, GJA1P1 gene extracted from Human Hanukah factor serine protease (HuHF) mRNA, complete cds" |
| M19045_f_at | "M19045, class A, 20 probes, 20 in M19045 907-1414, Human lysozyme mRNA, complete cds" |
| M19481_at | "M19481, class C, 20 probes, 14 in all_M19481 278-651: 6 in M19481cds 818-921, Human follistatin gene" |
| M19645_at | "M19645, class C, 20 probes, 20 in all_M19645 4941-5470, Human 78 kdalton glucose-regulated protein (GRP78) gene, complete cds" |
| M19720_ma2_at | "M19720, class A, 20 probes, 20 in M19720mRNA#2 2659-3217, L-myc gene (L-myc protein) extracted from Human L-myc protein gene, complete cds, L-myc gene (L-myc protein) extracted from Human L-myc protein gene, complete cds" |
| M19888_at | "M19888, class A, 20 probes, 20 in M19888 58-580, Human small proline rich protein (sprI) mRNA, clone 128" |
| M21121_at | "M21121, class A, 20 probes, 20 in M21121 958-1129, Human T cell-specific protein (RANTES) mRNA, complete cds" |
| M21389_at | "M21389, class A, 20 probes, 20 in M21389mRNA 1754-2192, Human keratin type II (58 kD) mRNA, complete cds" |
| M22995_at | "M22995, class A, 20 probes, 20 in M22995 1008-1542, Human ras-related protein (Krev-I) mRNA, complete cds" |
| M23294_at | "M23294, class A, 20 probes, 20 in M23294mRNA#1 1219-1651, Human beta-hexosaminidase beta-subunit (HEXB) gene" |
| M24194_at | "M24194, class A, 20 probes, 20 in M24194mRNA 504-1023, Human MHC protein homologous to chicken B complex protein mRNA, complete cds" |
| M24351_cds2_at | "M24351, class C, 20 probes, 20 not in GB record, PTHLH gene (parathyroid hormone-like protein A) extracted from Human parathyroid hormone-like protein (PLP) gene, PTHLH gene (parathyroid hormone-like protein A) extracted from Human parathyroid hormone-lik" |
| M24351_cds3_s_at | "M24351, class A, 20 probes, 20 in M24351exon 248-404, PTHLH gene (parathyroid hormone-like protein A) extracted from Human parathyroid hormon" |
| M24486_s_at | "M24486, class A, 20 probes, 20 in M24486mRNA 2110-2684, Human prolyl 4-hydroxylase alpha subunit mRNA, complete cds" |
| M24594_at | "M24594, class A, 20 probes, 20 in M24594mRNA 1077-1593, Human interferon-inducible 56 Kd protein mRNA, complete cds" |
| M24902_at | "M24902, class A, 20 probes, 20 in M24902mRNA 2694-3018, Human prostatic acid phosphatase mRNA, complete cds" |
| M25079_s_at | "M25079, class A, 20 probes, 20 in M25079 163-230, Human sickle cell beta-globin mRNA, complete cds" |
| M26311_s_at | "M26311, class A, 19 probes, 19 in M26311 27-504, Human cystic fibrosis antigen mRNA, complete cds." |
| M26576_cds2_at | "M26576, class B, 20 probes, 10 in M26576exon 43-289: 10 not in GB record, COL4A1 gene (alpha-I type IV collagen) extracted from Human alpha-I collagen type IV gene" |
| M27160_at | "M27160, class A, 20 probes, 20 in M27160mRNA 1441-1879, Human tyrosinase (TYR) mRNA, complete cds" |

FIGURE 7E

| Probe ID | Description |
|---|---|
| M29064_at | "M29064, class A, 20 probes, 20 in M29064 1225-1657, Human hnRNP B1 protein mRNA" |
| M29540_at | "M29540, class A, 20 probes, 20 in M29540 2616-2949, Human carcinoembryonic antigen mRNA (CEA), complete cds" |
| M30257_s_at | "M30257, class A, 20 probes, 20 in M30257 2214-2709, Human vascular cell adhesion molecule 1 mRNA, complete cds" |
| M30818_at | "M30818, class A, 20 probes, 20 in M30818mRNA 2384-2888, Human interferon-induced cellular resistance mediator protein (MxB) mRNA, complete cds" |
| M31551_s_at | "M31551, class C, 20 probes, 20 in all_M31551 576-1134, Human urokinase inhibitor (PAI-2) gene" |
| M31627_at | "M31627, class A, 20 probes, 20 in M31627 1191-1725, Human X box binding protein-1 (XBP-1) mRNA, complete cds" |
| M31642_at | "M31642, class A, 20 probes, 20 in M31642mRNA 802-1288, Human hypoxanthine phosphoribosyltransferase (HPRT) mRNA, complete cds" |
| M31994_at | "M31994, class C, 20 probes, 20 in all_M31994 117-538, Human cytosolic aldehyde dehydrogenase (ALDH1) gene" |
| M32011_at | "M32011, class A, 20 probes, 20 in M32011mRNA 1623-2157, Human neutrophil oxidase factor (p67-phox) mRNA, complete cds" |
| M32402_at | "M32402, class A, 20 probes, 20 in M32402mRNA 1851-2253, Human placental protein (PP11) mRNA, complete cds" |
| M33764_at | "M33764, class B, 20 probes, 12 in M33764cds 1158-1350: 8 in reverseSequence, 7989-8235, Human ornithine decarboxylase gene, complete cds" |
| M33882_at | "M33882, class A, 20 probes, 20 in M33882 2348-2762, Human p78 protein mRNA, complete cds" |
| M34057_at | "M34057, class A, 20 probes, 20 in M34057 4720-5044, Human transforming growth factor-beta 1 binding protein mRNA, complete cds" |
| M34309_at | "M34309, class A, 20 probes, 20 in M34309 4410-4836, Human epidermal growth factor receptor (HER3) mRNA, complete cds" |
| M34423_at | "M34423, class A, 20 probes, 20 in M34423 1856-2312, Human beta-galactosidase (GLB1) mRNA, complete cds" |
| M34516_r_at | "M34516, class C, 11 probes, 11 in all_M34516 426-469, Human omega light chain protein 14.1 (Ig lambda chain related) gene, Human omega light chain protein 14.1 (Ig lambda chain related) gene" |
| M35878_at | "M35878, class A, 20 probes, 20 in M35878exon#4 1993-2443, Human insulin-like growth factor-binding protein-3 gene, complete cds, clone HL1006d" |
| M36341_at | "M36341, class A, 20 probes, 20 in M36341 912-1458, Human ADP-ribosylation factor 4 (ARF4) mRNA, complete cds" |
| M37721_at | "M37721, class A, 20 probes, 20 in M37721 3297-3705, Human peptidylglycine alpha-amidating monooxygenase mRNA, complete cds" |
| M37766_at | "M37766, class A, 20 probes, 20 in M37766 475-955, Human MEM-102 glycoprotein mRNA, complete cds" |
| M55542_at | "M55542, class A, 20 probes, 20 in M55542mRNA 2310-2802, Human guanylate binding protein isoform I (GBP-2) mRNA, complete cds" |
| M55998_s_at | "M55998, class C, 20 probes, 20 in all_M55998 2-265, Human alpha-1 collagen type I gene, 3' end" |
| M57710_at | "M57710, class A, 20 probes, 20 in M57710 355-865, Human IgE-binding protein (epsilon-BP) mRNA, complete cds" |
| M57731_s_at | "M57731, class C, 20 probes, 20 in M57731mRNA 617-1032, Human gro-beta mRNA, complete cds" |
| M59465_at | "M59465, class A, 20 probes, 20 in M59465 3867-4341, Human tumor necrosis factor alpha inducible protein A20 mRNA, complete cds" |
| M61853_at | "M61853, class C, 20 probes, 20 in all_M61853 1735-2240, Human cytochrome P4502C18 (CYP2C18) mRNA, clone 6b" |
| M61855_at | "M61855, class C, 20 probes, 20 in all_M61855 1535-1714, Human cytochrome P4502C9 (CYP2C9) mRNA, clone 25" |
| M61906_at | "M61906, class A, 20 probes, 20 in M61906 2813-3326, Human P13-kinase associated p85 mRNA sequence" |
| M62982_at | "M62982, class A, 20 probes, 20 in M62982 1795-2299, Human arachidonate 12-lipoxygenase mRNA, complete cds" |
| M63256_at | "M63256, class A, 20 probes, 20 in M63256 1975-2497, Human major Yo paraneoplastic antigen (CDR2) mRNA, 3' end" |
| M63438_s_at | "M63438, class A, 17 probes, 17 in M63438 794-1195, Human Ig rearranged gamma chain mRNA, V-J-C region and complete cds" |
| M63835_at | "M63835, class A, 20 probes, 20 in M63835mRNA 896-1388, Human IgG Fc receptor I gene" |
| M64082_at | "M64082, class A, 20 probes, 20 in M64082 1605-2055, Human flavin-containing monooxygenase (FMO1) mRNA, complete cds" |
| M64347_at | "M64347, class A, 20 probes, 20 in M64347 3336-3720, Human novel growth factor receptor mRNA, 3' cds" |
| M64929_at | "M64929, class A, 20 probes, 20 in M64929 1572-2100, Human protein phosphatase 2A alpha subunit mRNA, complete cds" |
| M65292_s_at | "M65292, class A, 20 probes, 20 in M65292 667-1202, Human factor H homologue mRNA, complete cds" |
| M69177_at | "M69177, class A, 20 probes, 20 in M69177 1992-2436, Human monoamine oxidase B (MAOB) mRNA, complete cds" |
| M69181_at | "M69181, class A, 20 probes, 20 in M69181 6995-7523, Human nonmuscle myosin heavy chain-B (MYH10) mRNA, partial cds" |
| M76482_at | "M76482, class A, 20 probes, 20 in M76482 2855-3251, Human 130-kD pemphigus vulgaris antigen mRNA, complete cds" |
| M77349_at | "M77349, class A, 20 probes, 20 in M77349 2102-2642, Human transforming growth factor-beta induced gene product (BIGH3) mRNA, complete cds" |
| M81182_s_at | "M81182, class A, 20 probes, 20 in M81182 2831-3314, Homo sapiens peroxisomal 70 kD membrane protein mRNA, complete cds" |

FIGURE 7F

M83186_at "M83186, class A, 20 probes, 20 in M83186 103-316, Human cytochrome c oxidase subunit VIIa (COX7A) muscle isoform mRNA, complete cds"
M83667_mal_s_at "M83667, class A, 20 probes, 20 in M83667mRNA 713-1143, Human NF-IL6-beta protein mRNA, complete cds"
M83822_at "M83822, class A, 20 probes, 20 in M83822 6791-7253, Human beige-like protein (BGL) mRNA, partial cds"
M86699_at "M86699, class A, 20 probes, 20 in M86699 3355-3787, Human kinase (TTK) mRNA, complete cds"
M87789_s_at "M87789, class A, 20 probes, 20 in M87789 1021-1512, Human (hybridoma H210) anti-hepatitis A IgG variable region, constant region, complementarity-determining regions mRNA, complete cds"
M88458_at "M88458, class A, 20 probes, 20 in M88458 585-1095, Human ELP-1 mRNA sequence"
M93036_at "M93036, class A, 20 probes, 18 in M93036mRNA 987-1353: 2 in reverseSequence, 527-545, Human (clone 21726) carcinoma-associated antigen GA733-2 (GA733-2) mRNA"
M93056_at "M93056, class A, 20 probes, 20 in M93056 859-1273, Human monocyte/neutrophil elastase inhibitor mRNA sequence"
M93221_at "M93221, class A, 20 probes, 20 in M93221mRNA 4618-5110, Human macrophage mannose receptor (MRC1) gene"
M93426_at "M93426, class A, 20 probes, 20 in M93426 7455-7845, Human protein tyrosine phosphatase zeta-polypeptide (PTPRZ) mRNA, complete cds"
M96740_at "M96740, class A, 20 probes, 20 in M96740 2014-2476, Human NSCL-2 gene sequence"
M97935_s_at "M97935, class A, 20 probes, 20 in M97935 3412-3886, Human transcription factor ISGF-3 mRNA sequence"
M97936_at "M97936, class A, 20 probes, 20 in M97936 2354-2564, Human transcription factor ISGF-3 mRNA sequence"
M98447_mal_at "M98447, class A, 20 probes, 20 in M98447mRNA 2256-2670, H.sapiens keratinocyte transglutaminase gene, complete cds"
M98776_mal_at "M98776, class A, 20 probes, 20 in M98776mRNA 1864-2266, Human keratin 1 gene, complete cds"
S45630_at "S45630, class A, 20 probes, 20 in S45630 108-612, alpha B-crystallin=Rosenthal fiber component [human, glioma cell line, mRNA, 691 nt]"
S54005_s_at "S54005, class A, 20 probes, 20 in S54005 2-197, thymosin beta-10 [human, metastatic melanoma cell line, mRNA, 453 nt]"
S59049_at "S59049, class A, 20 probes, 20 in S59049 786-1314, BL34=B cell activation gene [human, mRNA, 1398 nt]"
S62539_at "S62539, class A, 20 probes, 20 in S62539 5366-5756, insulin receptor substrate-1 [human, skeletal muscle, mRNA, 5828 nt]"
S67156_at "S67156, class A, 20 probes, 20 in S67156 876-1368, ASP=aspartoacylase [human, kidney, mRNA, 1435 nt]"
S68805_at "S68805, class A, 20 probes, 20 in S68805 1972-2305, L-arginine:glycine amidinotransferase [human, kidney carcinoma cells, mRNA, 2330 nt]"
S69232_at "S69232, class A, 20 probes, 20 in S69232 1584-1992, electron transfer flavoprotein-ubiquinone oxidoreductase [human, fetal liver, mRNA, 2124 nt]"
S73591_at "S73591, class A, 20 probes, 20 in S73591 2169-2649, brain-expressed HHCPA78 homolog [human, HL-60 acute promyelocytic leukemia cells, mRNA, 2704 nt]"
S74017_at "S74017, class A, 20 probes, 20 in S74017 1721-2213, Nrf2=NF-E2-like basic leucine zipper transcriptional activator [human, hemin-induced K562 cells, mRNA, 2304 nt]"
S74728_at "S74728, class A, 20 probes, 20 in S74728 1245-1773, antiquitin=26g turgor protein homolog [human, kidney, mRNA, 1809 nt]"
S78187_at "S78187, class A, 20 probes, 20 in S78187 2548-3064, CDC25Hu2=cdc25+ homolog [human, mRNA, 3118 nt]"
S78569_at "S78569, class A, 20 probes, 20 in S78569 5723-6161, laminin alpha 4 chain [human, fetal lung, mRNA, 6204 nt]"
S82597_mal_s_at "S82597, class A, 20 probes, 20 in S82597mRNA 9-507, Description: UDP-GalNAc:polypeptide N-acetylgalactosaminyltransferase gene extracted from UDP-GalNAc:polypeptide N-acetylgalactosaminyltransferase/GalNAc-transferase {3' region, exon 11} [human, placent"
U02020_at "U02020, class C, 20 probes, 20 in all_U02020 1985-2352, Human pre-B cell enhancing factor (PBEF) mRNA, complete cds"
U02556_at "U02556, class A, 20 probes, 20 in U02556 1579-2101, Human RP3 mRNA, complete cds"
U03272_at "U03272, class A, 20 probes, 20 in U03272 9619-10081, Human fibrillin-2 mRNA, complete cds"
U04898_at "U04898, class A, 20 probes, 20 in U04898 1421-1877, Human orphan hormone nuclear receptor RORalpha2 mRNA, complete cds"
U05861_at "U05861, class B, 20 probes, 15 in U05861exon 50-243: 5 not in GB record, Human hepatic dihydrodiol dehydrogenase gene"
U06643_s_at "U06643, class A, 19 probes, 19 in U06643 71-463, Human keratinocyte lectin 14 (HKL-14) mRNA, complete cds."
U07919_at "U07919, class A, 20 probes, 20 in U07919 2973-3399, Human aldehyde dehydrogenase 6 mRNA, complete cds"
U09278_at "U09278, class A, 20 probes, 20 in U09278 2285-2735, Human fibroblast activation protein mRNA, complete cds"
U09578_at "U09578, class A, 20 probes, 20 in U09578 2012-2456, Human MAPKAP kinase (3pK) mRNA, complete cds"

FIGURE 7G

| | | |
|---|---|---|
| U09770_at | "U09770, class A, 20 probes, 20 in U09770 61-391, Human cysteine-rich heart protein (hCRHP) mRNA, complete cds" |
| U12767_at | "U12767, class A, 20 probes, 20 in U12767 4598-4922, Human mitogen induced nuclear orphan receptor (MINOR) mRNA, complete cds" |
| U13737_at | "U13737, class A, 20 probes, 20 in U13737 2046-2556, Human cysteine protease CPP32 isoform alpha mRNA, complete cds" |
| U14518_at | "U14518, class A, 20 probes, 20 in U14518 859-1315, Human centromere protein-A (CENP-A) mRNA, complete cds" |
| U14970_at | "U14970, class A, 20 probes, 20 in U14970 122-656, Human ribosomal protein S5 mRNA, complete cds" |
| U15932_at | "U15932, class A, 20 probes, 20 in U15932 1928-2294, Human dual-specificity protein phosphatase mRNA, complete cds" |
| U16306_at | "U16306, class A, 20 probes, 20 in U16306 10722-11142, Human chondroitin sulfate proteoglycan versican V0 splice-variant precursor peptide mRNA, complete cds" |
| U16799_s_at | "U16799, class A, 20 probes, 20 in U16799 865-1419, Human Na,K-ATPase beta-1 subunit mRNA, complete cds" |
| U17077_at | "U17077, class A, 20 probes, 20 in U17077 1716-2190, Human BENE mRNA, partial cds" |
| U18062_at | "U18062, class A, 20 probes, 20 in U18062 1678-2152, Human TFIID subunit TAFII55 (TAFII55) mRNA, complete cds" |
| U18934_at | "U18934, class A, 20 probes, 20 in U18934 4229-4311, Human receptor tyrosine kinase (DTK) mRNA, complete cds" |
| U20158_at | "U20158, class A, 20 probes, 20 in U20158 1551-1911, Human 76 kDa tyrosine phosphoprotein SLP-76 mRNA, complete cds" |
| U20758_mal_at | "U20758, class A, 20 probes, 20 in U20758mRNA 885-1437, Human osteopontin gene, complete cds" |
| U21128_at | "U21128, class A, 20 probes, 20 in U21128 1254-1632, Human lumican mRNA, complete cds" |
| U23942_at | "U23942, class A, 20 probes, 20 in U23942 2811-3129, Human lanosterol 14-demethylase cytochrome P450 (CYP51) mRNA, complete cds" |
| U24166_at | "U24166, class A, 20 probes, 20 in U24166 2107-2395, Human EB1 mRNA, complete cds" |
| U24577_at | "U24577, class A, 20 probes, 20 in U24577 1182-1512, Human LDL-phospholipase A2 mRNA, complete cds" |
| U25182_at | "U25182, class A, 20 probes, 20 in U25182 350-860, Human antioxidant enzyme AOE37-2 mRNA, complete cds" |
| U26312_s_at | "U26312, class A, 20 probes, 20 in U26312 166-686, Human heterochromatin protein HP1Hs-gamma mRNA, complete cds" |
| U27326_s_at | "U27326, class A, 20 probes, 20 in U27326 1666-2123, Human alpha (1,3/1,4) fucosyltransferase (FUT3) mRNA, major transcript I, complete cds" |
| U27333_s_at | "U27333, class C, 9 probes, 9 in all_U27333 2701-2753, Human alpha (1,3) fucosyltransferase (FUT6) mRNA, major transcript I, complete cds, Human alpha (1,3) fucosyltransferase (FUT6) mRNA, major transcript I, complete cds" |
| U28488_s_at | "U28488, class A, 20 probes, 20 in U28488 1344-1847, Human putative G protein-coupled receptor (AZ3B) mRNA, complete cds" |
| U31201_cds2_s_at | "U31201, class A, 20 probes, 20 in U31201mRNA 4592-5106, Human laminin gamma2 chain gene (LAMC2), Human laminin gamma2 chain gene (LAMC2)" |
| U31556_at | "U31556, class A, 20 probes, 20 in U31556 1445-1679, Human transcription factor E2F-5 mRNA, complete cds" |
| U32849_at | "U32849, class A, 20 probes, 20 in U32849 867-1383, Human Hou mRNA, complete cds" |
| U34252_at | "U34252, class A, 20 probes, 20 in U34252 2177-2579, Human gamma-aminobutyraldehyde dehydrogenase mRNA, complete cds" |
| U37518_at | "U37518, class A, 20 probes, 20 in U37518 1162-1390, Human TNF-related apoptosis inducing ligand TRAIL mRNA, complete cds" |
| U37519_at | "U37519, class A, 20 probes, 20 in U37519 2304-2784, Human aldehyde dehydrogenase (ALDH8) mRNA, complete cds" |
| U38545_at | "U38545, class A, 20 probes, 20 in U38545 3056-3578, Human ARF-activated phosphatidylcholine-specific phospholipase D1a (hPLD1) mRNA, complete cds" |
| U39318_at | "U39318, class A, 20 probes, 20 in U39318 159-675, Human E2 ubiquitin conjugating enzyme UbcH5C (UBCH5C) mRNA, complete cds" |
| U40622_at | "U40622, class A, 20 probes, 20 in U40622 999-1449, Human XRCC4 mRNA, complete cds" |
| U41060_at | "U41060, class A, 20 probes, 20 in U41060 2936-3416, Human breast cancer, estrogen regulated LIV-1 protein (LIV-1) mRNA, partial cds" |
| U43944_at | "U43944, class A, 20 probes, 20 in U43944 1705-1978, Human breast cancer cytosolic NADP(+)-dependent malic enzyme mRNA, partial cds" |
| U46499_at | "U46499, class C, 20 probes, 20 not in GB record, Human microsomal glutathione transferase (GST12) gene, 5' sequence" |
| U46689_at | "U46689, class A, 20 probes, 20 in U46689 3317-3863, Human microsomal aldehyde dehydrogenase (ALD10) mRNA, complete cds" |
| U46692_mal_at | "U46692, class A, 20 probes, 20 in U46692mRNA 84-480, Human cystatin B gene, complete cds" |
| U48705_mal_s_at | "U48705, class A, 20 probes, 20 in U48705mRNA 3326-3867, Human receptor tyrosine kinase DDR gene, complete cds" |
| U49114_at | "U49114, class A, 20 probes, 20 in U49114 2196-2700, Human prohormone convertase 5 precursor (PC5) mRNA, partial cds" |

FIGURE 7H

| Probe ID | Description |
|---|---|
| U50648_s_at | "U50648, class A, 20 probes, 20 in U50648mRNA 2211-2751, Human interferon-inducible RNA-dependent protein kinase (Pkr) gene" |
| U53446_at | "U53446, class A, 20 probes, 20 in U53446 2680-3220, Human mitogen-responsive phosphoprotein DOC-2 mRNA, complete cds" |
| U53506_at | "U53506, class A, 20 probes, 20 in U53506 1344-1836, Human type II iodothyronine deiodinase mRNA, complete cds." |
| U55206_at | "U55206, class A, 20 probes, 18 in U55206 790-1222: 2 not in GB record, Human gamma-glutamyl hydrolase (hGH) mRNA, complete cds" |
| U56814_at | "U56814, class A, 20 probes, 20 in U56814 495-957, Human DNAse I homologous protein (DHP2) mRNA, complete cds" |
| U57721_at | "U57721, class A, 20 probes, 20 in U57721 1126-1588, Human L-kynurenine hydrolase mRNA, complete cds" |
| U59877_s_at | "U59877, class A, 20 probes, 20 in U59877 295-750, Human low-Mr GTP-binding protein (RAB31) mRNA, complete cds" |
| U60060_at | "U60060, class A, 20 probes, 20 in U60060 1090-1540, Human FEZ1 mRNA, complete cds" |
| U60115_at | "U60115, class A, 20 probes, 20 in U60115 1863-2211, Human skeletal muscle LIM-protein SLIM1 mRNA, complete cds" |
| U60808_s_at | "U60808, class A, 20 probes, 20 in U60808 1423-2000, Human CDP-diacylglycerol synthase (CDS) mRNA, complete cds." |
| U62800_at | "U62800, class A, 20 probes, 20 in U62800 181-535, Human cystatin M (CST6) mRNA, complete cds" |
| U63743_at | "U63743, class A, 20 probes, 20 in U63743 2187-2715, Human mitotic centromere-associated kinesin mRNA, complete cds." |
| U65932_at | "U65932, class A, 20 probes, 20 in U65932 1244-1634, Human extracellular matrix protein 1 (ECM1) mRNA, complete cds" |
| U67122_s_at | "U67122, class A, 20 probes, 20 in U67122 469-728, Human ubiquitin-related protein SUMO-1 mRNA, complete cds." |
| U67784_at | "U67784, class A, 20 probes, 20 in U67784 1106-1640, Human orphan G protein-coupled receptor (RDC1) mRNA, partial cds" |
| U67963_at | "U67963, class A, 20 probes, 20 in U67963 590-1148, Human lysophospholipase homolog (HU-K5) mRNA, complete cds" |
| U68142_at | "U68142, class A, 20 probes, 20 in U68142 1372-1900, Human RalGDS-like 2 (RGL2) mRNA, partial cds" |
| U69961_at | "U69961, class A, 20 probes, 20 in U69961 1565-1997, Human solurshin (RGS) mRNA, complete cds" |
| U71207_at | "U71207, class A, 20 probes, 20 in U71207 1846-2224, Human eyes absent homolog (Eab1) mRNA, complete cds." |
| U72621_at | "U72621, class A, 20 probes, 20 in U72621 2581-3145, Human p66shc (SHC) mRNA, complete cds." |
| U73377_at | "U73377, class A, 20 probes, 20 in U73377 3059-3363, Human ADP-ribosylation factor-like protein 4 mRNA, complete cds" |
| U73960_at | "U73960, class A, 20 probes, 20 in U73960 566-1022, Human microsomal glutathione S-transferase (GST-II) mRNA, complete cds" |
| U77604_at | "U77604, class A, 20 probes, 20 in U77604 13-493, Human eukaryotic translation initiation factor (eIF3) mRNA, complete cds" |
| U78525_at | "U78525, class A, 20 probes, 20 in U78525 2480-2942, Human tumor susceptiblity protein (TSG101) mRNA, complete cds" |
| U82130_at | "U82130, class A, 20 probes, 20 in U82130 1151-1451, Human non-lens beta gamma-crystallin like protein (AIM1) mRNA, partial cds" |
| U83115_at | "U83115, class A, 20 probes, 20 in U83115 6327-6753, Homo sapiens lysyl hydroxylase isoform 2 (PLOD2) mRNA, complete cds" |
| U84573_at | "U84573, class A, 20 probes, 20 in U84573 2882-3422, Human transcription factor ERF-1 mRNA, complete cds" |
| U85658_at | "U85658, class A, 20 probes, 20 in U85658 2310-2736, Human leukemogenic homolog protein (MEIS1) mRNA, complete cds" |
| U85707_at | "U85707, class A, 20 probes, 20 in U85707 1922-2426, Human HEM45 mRNA, complete cds." |
| U88964_at | "U88964, class A, 20 probes, 20 in U88964 130-568, Human lysyl oxidase-related protein (WS9-14) mRNA, complete cds" |
| U89942_at | "U89942, class A, 20 probes, 20 in U89942 2867-3383, Human butyrophilin (BTF4) mRNA, complete cds, Human butyrophilin (BTF4) mRNA, complete cds" |
| U90546_at | "U90546, class B, 12 probes, 12 in U90546 1301-1344, Human clone 23612 mRNA sequence" |
| U90902_at | "U90902, class A, 20 probes, 20 in U90902 939-1407, Human clone 23773 mRNA sequence" |
| U90904_at | "U90904, class A, 20 probes, 20 in U90904 1102-1342, Homo sapiens sin3 associated polypeptide p18 (SAP18) mRNA, complete cds." |
| U96915_at | "U96915, class A, 20 probes, 20 in U96915 165-693, IFNG gene extracted from Human immune interferon (IFN-gamma) gene" |
| V00536_mal_at | "V00536, class A, 20 probes, 20 in V00536mRNA 811-1135, Human gene for immunoglobulin mu, part of exon 8." |
| V00563_at | "V00563, class A, 20 probes, 20 in V00563mRNA 19-127, Human mRNA for transferrin receptor" |
| X01060_at | "X01060, class C, 20 probes, 20 in all_X01060 4427-4986, Human mRNA for transferrin receptor" |
| X02419_mal_s_at | "X02419, class A, 20 probes, 20 in X02419mRNA 1754-2210, H.sapiens uPA gene" |
| X02530_at | "X02530, class C, 20 probes, 20 in all_X02530 571-1118, Human mRNA for gamma-interferon inducible early response gene (with homology to platelet proteins)" |

FIGURE 7I

| | | |
|---|---|---|
| X02761_s_at | "X02761, class C, 20 probes, 20 in all_X02761 7082-7646, Human mRNA for fibronectin (FN precursor)" |
| X02875_s_at | "X02875, class C, 20 probes, 20 in all_X02875 158-628, Human mRNA (3'-fragment) for (2'-5') oligo A synthetase E (1,8 kb RNA)" |
| X04470_s_at | "X04470, class B, 19 probes, 15 in X04470cds 24-374: 4 in reverseSequence, 408-495, Human mRNA for antileukoprotease (ALP) from cervix uterus" |
| X04602_s_at | "X04602, class C, 20 probes, 20 in all_X04602 920-1086, Human mRNA for interleukin BSF-2 (B-cell differentiation factor)" |
| X05232_s_at | "X05232, class C, 20 probes, 20 in all_X05232 1530-1771, Human mRNA for stromelysin" |
| X05610_at | "X05610, class C, 20 probes, 20 in all_X05610 1701-2098, Human mRNA for type IV collagen alpha-2 chain" |
| X06700_s_at | "X06700, class C, 20 probes, 20 in all_X06700 1946-2466, Human mRNA 3' region for pro-alpha1(III) collagen" |
| X06948_at | "X06948, class B, 20 probes, 12 in X06948cds 482-680: 8 in reverseSequence, 918-1146, Human mRNA for high affinity IgE receptor alpha-subunit (FcERI)" |
| X07109_at | "X07109, class C, 20 probes, 20 in all_X07109 2732-3303, Human mRNA for protein kinase C (PKC) type beta II" |
| X07438_s_at | "X07438, class A, 19 probes, 19 in X07438exon#2 11-166, Human DNA for cellular retinol binding protein (CRBP) exons 3 and 4 /gb=X07438 /ntype=DNA /annot=exon" |
| X07695_at | "X07695, class C, 20 probes, 20 in all_X07695 1175-1722, Human mRNA for cytokeratin 4 C-terminal region" |
| X07696_at | "X07696, class C, 20 probes, 20 in all_X07696 1300-1685, Human mRNA for cytokeratin 15" |
| X07834_at | "X07834, class C, 20 probes, 20 in all_X07834 515-1026, Human mRNA for manganese superoxide dismutase (EC 1.15.1.1)" |
| X12451_at | "X12451, class A, 20 probes, 20 in X12451mRNA 974-1496, Human mrRNA for pro-cathepsin L (major excreted protein MEP)" |
| X13794_mal_at | "X13794, class A, 20 probes, 20 in X13794mRNA 713-1229, H.sapiens lactate dehydrogenase B gene exon 1 and 2 (EC 1.1.1.27) (and joined CDS)" |
| X13839_at | "X13839, class C, 20 probes, 20 in all_X13839 768-1300, Human mRNA for vascular smooth muscle alpha-actin" |
| X14008_mal_f_at | "X14008, class A, 20 probes, 20 in X14008mRNA 926-1433, Human lysozyme gene (EC 3.2.1.17)" |
| X14813_at | "X14813, class C, 20 probes, 20 in all_X14813 1077-1618, Human liver mRNA for 3-oxoacyl-CoA thiolase" |
| X15183_at | "X15183, class C, 20 probes, 20 in all_X15183 2479-2894, Human mRNA for 90-kDa heat-shock protein" |
| X15187_at | "X15187, class B, 20 probes, 10 in X15187cds 2089-2380: 10 in reverseSequence, 2521-2737, Human tra1 mRNA for human homologue of murine tumor rejection antigen gp96" |
| X15414_at | "X15414, class C, 20 probes, 20 in all_X15414 844-1349, Human mRNA for aldose reductase (EC 1.1.1.2)" |
| X16354_at | "X16354, class C, 20 probes, 20 in all_X16354 2895-3400, Human mRNA for transmembrane carcinoembryonic antigen BGPa (formerly TM1-CEA)" |
| X16396_at | "X16396, class C, 20 probes, 20 in all_X16396 1543-2102, Human mRNA for NAD-dependent methylene tetrahydrofolate dehydrogenase cyclohydrolase (EC 1.5.1.15)" |
| X16662_at | "X16662, class C, 20 probes, 20 in all_X16662 1399-1916, Human mRNA for vascular anticoagulant-beta (VAC-beta)" |
| X17042_at | "X17042, class C, 20 probes, 20 in all_X17042 689-1158, Human mRNA for hematopoetic proteoglycan core protein" |
| X51408_at | "X51408, class C, 20 probes, 20 in all_X51408 1626-2017, Human mRNA for n-chimaerin" |
| X51420_at | "X51420, class C, 20 probes, 20 in all_X51420 2264-2781, Human mRNA for tyrosinase-related protein" |
| X51441_at | "X51441, class B, 12 probes, 11 in X51441cds 28-65: 1 in reverseSequence, 228, Human mRNA for serum amyloid A (SAA) protein partial, clone pAS3-alpha, Human mRNA for serum amyloid A (SAA) protein partial, clone pAS3-alpha" |
| X51441_s_at | "X51441, class C, 8 probes, 8 in all_X51441 55-90, Human mRNA for serum amyloid A (SAA) protein partial, clone pAS3-alpha" |
| X51521_at | "X51521, class C, 20 probes, 20 in all_X51521 2653-3026, Human mRNA for ezrin" |
| X51801_at | "X51801, class C, 20 probes, 20 in all_X51801 1415-1824, Human OP-1 mRNA for osteogenic protein" |
| X52022_at | "X52022, class A, 20 probes, 20 in X52022 9941-10349, H.sapiens RNA for type VI collagen alpha3 chain" |
| X52426_at | "X52426, class C, 20 probes, 20 in all_X52426 1139-1665, H.sapiens mRNA for cytokeratin 13" |
| X53296_s_at | "X53296, class C, 20 probes, 20 in all_X53296 1099-1657, H.sapiens mRNA for IRAP" |
| X54489_mal_at | "X54489, class A, 20 probes, 20 in X54489mRNA 660-1034, Human gene for melanoma growth stimulatory activity (MGSA)" |
| X54867_s_at | "X54867, class A, 20 probes, 20 in X54867mRNA 783-1293, Human mRNA for NKG2-A gene" |

FIGURE 7J

| | | |
|---|---|---|
| X54925_at | "X54925, class C, 20 probes, 20 in all_X54925 1537-1904, H.sapiens mRNA for type I interstitial collagenase" |
| X54941_at | "X54941, class C, 20 probes, 20 in all_X54941 194-687, H.sapiens ckshs1 mRNA for Cks1 protein homologue" |
| X56654_at | "X56654, class A, 20 probes, 20 in X56654mRNA 3221-3641, Human DSG1 mRNA for desmoglein type 1" |
| X57522_at | "X57522, class C, 20 probes, 20 in all_X57522 2229-2788, H.sapiens RING4 cDNA" |
| X57579_s_at | "X57579, class A, 20 probes, 18 in X57579exon 545-840: 2 in reverseSequence, 1392-1555, H.sapiens activin beta-A subunit (exon 2)" |
| X59770_at | "X59770, class A, 20 probes, 20 in X59770mRNA 685-1213, H.sapiens IL-1R2 mRNA for type II interleukin-1 receptor, (cell line CB23)" |
| X59892_at | "X59892, class C, 20 probes, 20 in all_X59892 2163-2542, H.sapiens mRNA for IFN-inducible gamma2 protein" |
| X61123_at | "X61123, class A, 20 probes, 20 in X61123mRNA 1212-1608, Human BTG1 mRNA" |
| X61970_at | "X61970, class A, 20 probes, 17 in X61970cds 299-677: 3 in reverseSequence, 758-860, H.sapiens mRNA for macropain subunit zeta" |
| X63629_at | "X63629, class C, 20 probes, 20 in all_X63629 2582-3126, H.sapiens mRNA for p cadherin" |
| X64707_at | "X64707, class C, 20 probes, 20 in all_X64707 401-888, H.sapiens BBC1 mRNA" |
| X65614_at | "X65614, class B, 20 probes, 10 in X65614cds 10-262: 10 in reverseSequence, 19-391, H.sapiens mRNA for calcium-binding protein S100P" |
| X65965_s_at /annot=exon" | "X65965, class A, 18 probe, 18 in X65965exon#1-2 32-94, H.sapiens SOD-2 gene for manganese superoxide dismutase. /gb=X65965 /ntype=DNA |
| X66534_at | "X66534, class C, 20 probes, 20 in all_X66534 2622-2953, H.sapiens soluble guanylate cyclase large subunit mRNA" |
| X67098_at | "X67098, class A, 20 probes, 20 in X67098exon#8 40-454, H.sapiens rTS alpha mRNA containing four open reading frames" |
| X67951_at | "X67951, class B, 20 probes, 10 in X67951cds 312-576: 10 in reverseSequence, 642-888, H.sapiens mRNA for proliferation-associated gene (pag)" |
| X68277_at | "X68277, class C, 20 probes, 20 in all_X68277 1459-1952, H.sapiens CL 100 mRNA for protein tyrosine phosphatase" |
| X68742_at | "X68742, class C, 20 probes, 20 in all_X68742 2942-3423, H.sapiens mRNA for integrin, alpha subunit" |
| X69141_at | "X69141, class C, 20 probes, 20 in all_X69141 1444-1997, H.sapiens mRNA for squalene synthase" |
| X70476_at | "X70476, class A, 20 probes, 20 in X70476mRNA 2526-3024, H.sapiens subunit of coatomer complex" |
| X75252_at | "X75252, class C, 20 probes, 20 in all_X75252 1083-1408, H.sapiens phosphatidylethanolamine binding protein mRNA" |
| X76029_at | "X76029, class B, 20 probes, 14 in X76029cds 141-453: 6 in reverseSequence, 636-756, H.sapiens mRNA for neuromedin U" |
| X76180_at | "X76180, class C, 20 probes, 20 in all_X76180 2760-3115, H.sapiens mRNA for lung amiloride sensitive Na+ channel protein" |
| X76223_s_at | "X76223, class A, 20 probes, 20 in X76223exon 2-540, H.sapiens MAL gene exon 4," |
| X76342_at | "X76342, class C, 20 probes, 20 in all_X76342 1484-2019, H.sapiens ADH7 mRNA" |
| X76534_at | "X76534, class C, 20 probes, 20 in all_X76534 2145-2614, H.sapiens NMB mRNA" |
| X76648_at | "X76648, class C, 20 probes, 20 in all_X76648 338-777, H.sapiens mRNA for glutaredoxin" |
| X76732_at | "X76732, class B, 20 probes, 12 in X76732cds 975-1221: 6 in reverseSequence, 1464-1518: 2 not in GB record, H.sapiens mRNA for ATL-derived factor/thiredoxin" |
| X77584_at | "X77584, class B, 20 probes, 14 in X77584cds 5-215: 6 in reverseSequence, 43-481, H.sapiens mRNA for ATL-derived factor/thiredoxin" (DNA-binding leucine zipper protein, calcium-binding EF-hand protein, from acute lymphoblastic leukemia ce" |
| X78549_at | "X78549, class C, 20 probes, 20 in all_X78549 1912-2186, H.sapiens brk mRNA for tyrosine kinase" |
| X78565_at | "X78565, class C, 20 probes, 20 in all_X78565 6971-7512, H.sapiens mRNA for tenascin-C, 7560bp" |
| X78932_at | "X78932, class C, 20 probes, 20 in all_X78932 421-976, H.sapiens HZF9 mRNA for zinc finger protein" |
| X82153_at | "X82153, class C, 20 probes, 20 in all_X82153 1128-1615, H.sapiens mRNA for cathepsin O" |
| X82200_at | "X82200, class C, 20 probes, 20 in all_X82200 2236-2801, H.sapiens Staf50 mRNA" |
| X82693_at | "X82693, class C, 20 probes, 20 in all_X82693 134-681, H.sapiens mRNA for E48 antigen" |
| X85116_rna1_s_at | "X85116, class C, 20 probes, 20 not in GB record, H.sapiens epb72 gene exon 1" |
| X85750_at | "X85750, class C, 20 probes, 20 in all_X85750 1935-2500, H.sapiens mRNA for transcript associated with monocyte to macrophage differentiation" |
| X87212_at | "X87212, class C, 20 probes, 20 in all_X87212 1273-1772, H.sapiens mRNA for cathepsin C" |
| X87241_at | "X87241, class C, 20 probes, 20 in all_X87241 14353-14738, H.sapiens mRNA for hFat protein" |
| X91911_s_at | "X91911, class A, 20 probes, 18 in X91911cds 321-711: 2 in reverseSequence, 912-950, H.sapiens mRNA for RTVP-1 protein" |

FIGURE 7K

X95240_s_at "X95240, class C, 20 probes, 20 in all_X95240 1487-2056, H.sapiens mRNA for cysteine-rich secretory protein-3"
X96719_at "X96719, class A, 20 probes, 16 in X96719cds 86-398: 4 in reverseSequence, 674-710, H.sapiens mRNA for AICL (activation-induced C-type lectin)"
X98311_at "X98311, class C, 20 probes, 20 in all_X98311 1901-2274, H.sapiens mRNA for carcinoembryonic antigen, CGM2"
Y00264_at "Y00264, class C, 20 probes, 20 in all_Y00264 2984-3321, Human mRNA for amyloid A4 precursor of Alzheimer disease"
Y00787_s_at "Y00787, class C, 20 probes, 20 in all_Y00787 1314-1469, Human mRNA for MDNCF (monocyte-derived neutrophil chemotactic factor)"
Y00815_at "Y00815, class C, 20 probes, 20 in all_Y00815 7107-7684, Human mRNA for LCA-homolog. LAR protein (leukocyte antigen related)"
Y07759_at "Y07759, class C, 20 probes, 20 in all_Y07759 5956-6377, H.sapiens mRNA for myosin heavy chain 12"
Y07867_at "Y07867, class B, 20 probes, 11 in Y07867cds 643-787: 9 in reverseSequence, 1087-1237, H.sapiens mRNA for Pirin, isolate 1"
Y07909_at "Y07909, class C, 20 probes, 20 in all_Y07909 2383-2774, H.sapiens mRNA for Progression Associated Protein"
Y09267_at "Y09267, class A, 20 probes, 20 in Y09267 1148-1664, H.sapiens mRNA for flavin-containing monooxygenase 2 /gb=Y09267 /ntype=RNA"
Y09616_at "Y09616, class C, 20 probes, 20 in all_Y09616 1443-1948, H.sapiens mRNA for putative carboxylesterase"
Z15108_at "Z15108, class C, 20 probes, 20 in all_Z15108 1535-2130, H.sapiens mRNA for protein kinase C zeta"
Z19574_ma1_at "Z19574, class A, 20 probes, 20 in Z19574mRNA 1039-1479, H.sapiens gene for cytokeratin 17"
Z23090_at "Z23090, class A, 20 probes, 17 in Z23090cds 277-589: 3 in reverseSequence, 1086-1098, H.sapiens mRNA for 28 kDa heat shock protein"
Z24727_at "Z24727, class C, 20 probes, 20 in all_Z24727 1355-1569, H.sapiens tropomyosin isoform mRNA, complete CDS"
Z26491_s_at "Z26491, class A, 20 probes, 20 in Z26491exon#5 388-430, H.sapiens gene for catechol O-methyltransferase"
Z29083_at "Z29083, class C, 20 probes, 20 in all_Z29083 1644-2023, H.sapiens 5T4 gene for 5T4 Oncofetal antigen"
Z29574_at "Z29574, class A, 20 probes, 17 in Z29574exon#3 1-373: 1 in reverseSequence, 3141: 2 not in GB record, Homo sapiens gene for BCMA peptide"
Z47087_at "Z47087, class C, 20 probes, 20 in all_Z47087 1065-1438, H.sapiens mRNA for RNA polymerase II elongation factor-like protein"
Z48042_at "Z48042, class C, 20 probes, 20 in all_Z48042 2679-3232, H.sapiens mRNA encoding GPI-anchored protein p137"
Z49148_s_at "Z49148, class A, 20 probes, 16 in Z49148cds 2-418: 4 in reverseSequence, 18-589, H.sapiens mRNA for ribosomal protein L29"
Z49194_at "Z49194, class A, 20 probes, 20 in Z49194exon#5 1962-2256, H.sapiens mRNA for oct-binding factor"
Z74616_s_at "Z74616, class C, 20 probes, 20 in all_Z74616 4470-4992, H.sapiens mRNA for prepro-alpha2(I) collagen."
Z84721_cds2_at "Z84721, class C, 20 probes, 20 in all_Z84721 30317-34635, Human DNA sequence from cosmid GG1 from a contig from the tip of the short arm of chromosome 16, spanning 2Mb of 16p13.3 Contains alpha and zeta globin genes and ESTs., Human DNA sequence from cosm"

METHODS FOR DETECTING AND DIAGNOSING ORAL CANCER

RELATED APPLICATIONS

The present application claims priority to U.S. Provisional Application No. 60/231,057, filed on Sep. 8, 2000.

STATEMENT OF GOVERNMENT INTERESTS

This invention was made with Government support under NIH Grant No. P30DE011814 awarded by the National Institutes of Health Grant and the government has certain rights to the invention.

FIELD OF THE INVENTION

The present invention is in the field of diagnostics, detection or research analysis of cancer, and more particularly, oral cancer. More specifically, the present invention is in the field of analysis of the levels of gene expression in specific cancers using microarrays. Even more specifically, embodiments of the present invention are in the field of the identification of biological conditions characterized by alterations of the relative expression levels of various genes.

BACKGROUND

Many cellular events and processes are characterized by altered expression levels of one or more genes. Differences in gene expression correlate with many physiological processes such as cell cycle progression, cell differentiation and cell death. Changes in gene expression patterns also correlate with changes in disease or pharmacological state. For example, the lack of sufficient expression of functional tumor suppressor genes and/or the over expression of onco-gene/protooncogenes could lead to tumorgenesis (Marshall, Cell, 64: 313–326 (1991); Weinberg, Science, 254: 1138–1146 (1991), incorporated herein by reference in their entireties for all purposes). Thus, changes in the expression levels of particular genes (e.g. oncogenes or tumor suppressors) serve as signposts for different physiological, pharmacological and disease states.

Gene expression profiles produce a snapshot that reflects the biological status of the sample, but in many circumstances biological status will reflect more than one characteristic of the sample. For example, when comparing tumor samples from two patients, there will be changes that correlate with differences between the states of the tumors as well as changes that correlate with the different physiological states of the two patients. High-throughput technologies, such as DNA microarrays, have been used to profile and monitor gene expression of hematopoietic tumors (see Alizadeh et al., 2000; Golub et al., 1999 each incorporated by reference in their entireties for all purposes) and solid tumor homogenates and cell lines (see Alon et al., 1999, Perou et al., 2000, Sgroi et al., 1999 each incorporated by reference in their entireties for all purposes). However, the cell-specific profiling of solid tumor gene expression has been hampered by the inability to procure specific pure cell populations. A need exists to identify genes associated with normal and solid tumor cancerous cell conditions and to further correlate the expression levels of genes as a way of detecting or diagnosing a cancerous condition.

SUMMARY OF THE INVENTION

Embodiments of the present invention are directed to methods of detecting and/or diagnosing cancerous cell conditions, particularly oral cancerous cell conditions, and more particularly solid tumor oral cancerous cell conditions. According to one aspect of the present invention, the expression levels of genes obtained from malignant and non-malignant cell samples are identified and analyzed to provide a gene expression profile for malignant and non-malignant cells. According to one embodiment of the present invention, the expression levels of genes associated with a cell sample are identified and then analyzed and/or compared with known expression levels of genes for malignant and/or normal cells. Based upon similarities of expression levels of genes between the cell sample and malignant cells, a determination can be made as to whether the cell sample is malignant or not or may be predisposed to becoming malignant or not.

Embodiments of the present invention provide for the use of molecular profiling to distinguish normal and malignant oral tissues. Specifically, the present method is useful to diagnose or type oral cancer cells. According to the present invention, markers of malignant cells can be identified and used in diagnostic methods. One aspect of the current invention is directed at identifying genes that are differentially expressed between two biological states as being further correlated with disease, physiological or pharmacological state.

In a first aspect, a method of monitoring expression of one or more genes associated with oral cancer is provided. According to this method, a population of nucleic acids is prepared from a sample of cells obtained from malignant oral tissue. The nucleic acids are then contacted to an array of probes and the relative hybridization of the probes to the nucleic acids is determined. In a second aspect, a method of expression monitoring includes contacting a first array of probes with a first population of nucleic acids derived from at least one cell derived from normal tissue. A second array of probes is contacted with a second population of nucleic acids derived from at least one cell derived from malignant oral tissue. The relative binding of the probes to the nucleic acids from the first and second populations is then determined to identify at least one probe binding to a gene that is differentially expressed between the first and second populations.

According to the present invention, malignant oral cells can be classified by determining an expression profile of each of a plurality of cells derived from malignant oral tissue, and then classifying the cells in clusters determined by similarity of expression profile.

Embodiments of the present invention are also directed to a method of monitoring differentiation of a malignant oral cell lineage. According to this method, an expression profile of each of a plurality of cells derived from malignant oral tissue at different differentiation stages within the lineage is determined. The cells are classified in clusters determined by similarity of expression profile. The clusters are ordered by similarity of expression profile, and a time course of expression levels for each of the plurality of genes at different stages of differentiation in the malignant oral cell lineage is determined.

Embodiments of the present invention are also directed to a method for identifying differentially expressed transcripts associated with oral cancer. According to this method, an expression profile of each of a plurality of cells derived from malignant oral tissue at different differentiation stages within the lineage is determined. The cells are then classified in clusters determined by similarity of expression profile. The clusters are then ordered by similarity of expression profile, and then a time course of expression levels for each of the plurality of genes at different stages of differentiation in the cell lineage is determined. Differentially expressed transcripts are then identified.

Embodiments of the present invention are still further directed to a method of identifying an oral cancer-associated cell type wherein an expression profile of a plurality of cells derived from malignant oral tissue is determined. The cells are classified in clusters determined by similarity of expression profile, and then the nature and function of a plurality of cells is determined.

Embodiments of the present invention are even still further directed to a method of diagnosing a subject with oral cancer wherein nucleic acids are derived from a sample of tissue obtained from a subject. The level of expression of at least one gene or marker selected from a group of markers associated with oral cancer is determined. The level of expression of the at least one gene or marker is then compared with the normal level of expression of the marker in a control sample from normal tissue, wherein a difference of degree between the level of expression of the marker in the sample from the subject and the control sample from normal tissue indicates that the subject is afflicted with oral cancer.

A method for monitoring the progression of oral cancer in a subject is also provided wherein the expression of at least one gene or marker selected from a group of markers associated with oral cancer is determined from a sample of tissue taken from a subject at a first point in time. A second sample of tissue is taken at a subsequent point in time and the expression of the at least one gene or marker is determined. The levels of expression are then compared in a manner to monitor the progression of oral cancer.

Still further embodiments of the present invention are directed to a method of assessing the efficacy of a test compound for inhibiting oral cancer in a subject or the efficacy of a therapy for inhibiting oral cancer wherein the ability of a test compound of a therapy to inhibit expression of at least one gene or marker selected from a group of markers associated with oral cancer is determined by comparing the expression levels of the at least on gene or marker with and without the presence of the test compound or the therapy.

Similarly, compounds can be screened for their ability to inhibit oral cancer in a subject by obtaining a sample of cells from the subject, separately maintaining aliquots of the sample in the presence of a plurality of test compounds, comparing expression of at least one gene or marker selected from a group of markers associated with oral cancer in each of the aliquots, and selecting one of the test compounds based on its ability to alter the expression of the gene or marker.

Still, even further embodiments of the present invention are directed to a kit for assessing whether a subject is afflicted with oral cancer. The kit includes reagents and/or an array of probes for assessing expression of at least one gene or marker selected from a group of markers associated with oral cancer.

BRIEF DESCRIPTION OF THE DRAWINGS

FIG. 1A shows amounts of cDNA after two rounds of T7 amplification.

FIG. 1B shows percent transcripts detected in normal and tumor tissues.

FIG. 2A shows 39 genes whose expression changed in all five samples taken from patients participating in a pilot cancer study.

FIG. 2B shows a representative sample of the differentially expressed genes grouped into biological pathways known to be relevant in carcinogenesis FIG. 2C shows candidate genes that are up regulated.

FIG. 2D shows candidate genes that are down regulated.

FIG. 3 shows a comparison of percent increases for three upregulated genes measured by GENECHIP® and Real Time Quantitative PCR data.

FIG. 6 shows differentially expressed genes identified by three different methods.

FIGS. 7A–7K show differential gene expression using GENECHIP® analysis software which revealed that 404 genes are differentially expressed.

DETAILED DESCRIPTION OF CERTAIN PREFERRED EMBODIMENTS

Figure 4:
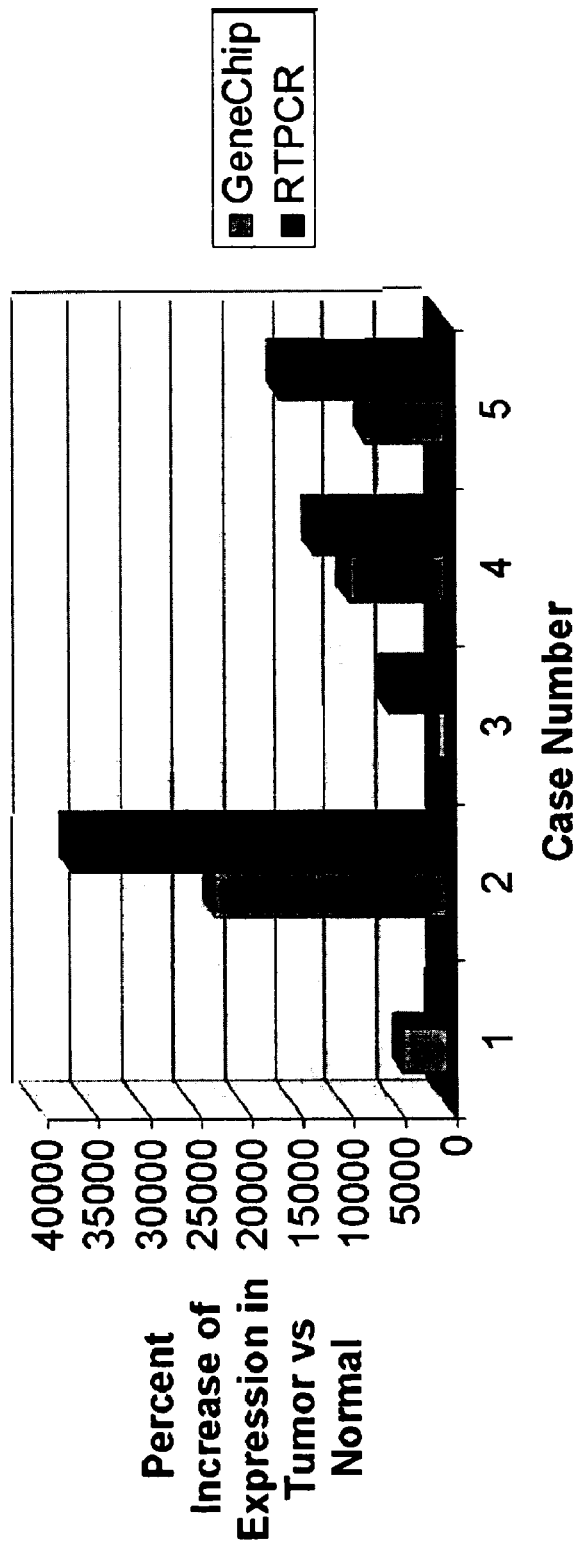
FIG. 4 shows a comparison of differential collagenase gene expression measured by GENECHIP® microarray and RT-QPCR.

This application relies on, and cites the disclosure of other patent applications and literature references. These documents are hereby incorporated by reference in their entireties for all purposes. The practice of the present invention may employ, unless otherwise indicated, conventional techniques of organic chemistry, polymer technology, molecular biology (including recombinant techniques), cell biology, biochemistry, and immunology, which are within the skill of the art. Such conventional techniques include polymer array synthesis, hybridization, ligation, detection of hybridization using a label. Specific illustrations of suitable techniques can be had by reference to the examples hereinbelow. However, other equivalent conventional procedures can, of course, also be used. Such conventional techniques can be found in standard laboratory manuals such as *Genome Analysis: A Laboratory Manual Series (Vols. I–IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), all of which are herein incorporated in their entirety by reference for all purposes.

This section presents a detailed description of the preferred invention and its application. This description is by way of several exemplary illustrations, in increasing detail and specificity, and of the general methods of this invention. These examples are non-limiting, and related variants that will be apparent to one of skill in the art are intended to be encompassed by the appended claims. Following these examples are descriptions of embodiments of the data gathering steps that accompany the general methods.

Principles of the present invention are directed to the molecular analysis of solid tumors and to providing methods for obtaining information about consistent molecular alterations that advance both the understanding of the basic biology of tumors as well as the clinically relevant aspects of the molecular epidemiology of oral cancer. In one aspect, the present invention incorporates the use of laser capture microdissection-derived RNA to be used on microarrays and that array hybridization coupled with hierarchical and nonhierarchical analysis methods provide powerful approaches for identifying candidate genes and molecular profiling associated with oral cancer.

Markers according to the present invention may include any nucleic acid sequence or molecule or corresponding polypeptide encoded by the nucleic acid sequence or molecule which demonstrates altered expression (i.e., higher or lower expression) in oral cancer samples relative to normal samples (i.e., non-oral cancer samples).

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Oligonucleotide and polynucleotide are included in this definition and relate to two or more nucleic acids in a polynucleotide.

Peptide: A polymer in which the monomers are alpha amino acids and which are joined together through amide bonds, alternatively referred to as a polypeptide and/or protein. In the context of this specification it should be appreciated that the amino acids may be, for example, the L-optical isomer or the D-optical isomer. Peptides are often two or more amino acid monomers long, and often 4 or more amino acids long, often 5 or more amino acids long, often 10 or more amino acids long, often 15 or more amino acids long, and often 20 or more amino acid monomers long, for example. Standard abbreviations for amino acids are used (e.g., P for proline). These abbreviations are included in Stryer, Biochemistry, Third Ed., 1988, which is incorporated herein by reference in its entirety for all purposes.

Array: An array comprises a solid support with peptide or nucleic acid probes attached to said support. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767–777 (1991). Each of which is incorporated by reference in its entirety for all purposes. These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261, and 6,040,193 which are incorporated herein by reference in their entirety for all purposes. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708, 153, 6,040,193 and 5,800,992, which are hereby incorporated by reference in their entirety for all purposes. Arrays may be packaged in such a manner as to allow for diagnostics or other manipulation of in an all inclusive device, see for example, U.S. Pat. Nos. 5,856,174 and 5,922,591 incorporated in their entirety by reference for all purposes. See also attorney docket number 3233.1 for additional information concerning arrays, their manufacture, and their characteristics. It is hereby incorporated by reference in its entirety for all purposes.

Gene expression monitoring is a useful way to distinguish between cells that express different phenotypes. For example, cells that are derived from different organs, have different ages, or different physiological states. In a preferred embodiment, gene expression monitoring can distinguish between cancer cells and normal cells, or different types of cancer cells.

Expression profile: One measurement of cellular constituents that is particularly useful in the present invention is the expression profile. As used herein, an "expression profile" comprises measurement of the relative abundance of a plurality of cellular constituents. Such measurements may include RNA or protein abundances or activity levels. An expression profile involves providing a pool of target nucleic acid molecules or polypeptides, hybridizing the pool to an array of probes immobilized on predetermined regions of a surface, and quantifying the hybridized nucleic acid molecules or proteins. The expression profile can be a measurement, for example, of the transcriptional state or the translational state of the cell. See U.S. Pat. Nos. 6,040,138, 6,013,449 and 5,800,992, which are hereby incorporated by reference in their entireties for all purposes.

Transcriptional state: The transcriptional state of a sample includes the identities and relative abundances of the RNA species, especially mRNAs present in the sample. Preferably, a substantial fraction of all constituent RNA species in the sample are measured, but at least a sufficient fraction is measured to characterize the state of the sample. The transcriptional state is the currently preferred aspect of the biological state measured in this invention. It can be conveniently determined by measuring transcript abundances by any of several existing gene expression technologies.

Translational state: Translational state includes the identities and relative abundances of the constituent protein species in the sample. As is known to those of skill in the art, the transcriptional state and translational state are related.

The gene expression monitoring system, in a preferred embodiment, may comprise a nucleic acid probe array (such as those described above), membrane blot (such as used in hybridization analysis such as Northern, Southern, dot, and the like), microwells, sample tubes, gels, beads or fibers (or any solid support comprising bound nucleic acids). See U.S. Pat. Nos. 5,770,722, 5,874,219, 5,744,305, 5,677,195 and 5,445,934, 5,800,992 which are expressly incorporated herein by reference in their entireties for all purposes.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue.

Differentially expressed: The term differentially expressed as used herein means that a measurement of a cellular constituent varies in two samples. The cellular constituent can be either upregulated in the experiment relative to the reference or downregulated in the experiment relative to the reference. Differential gene expression can also be used to distinguish between cell types or nucleic acids. See U.S. Pat. No. 5,800,992.

One of skill in the art will appreciate that it is desirable to have nucleic acid samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but are not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, a sample is a homogenate of cells (e.g., oral cells and/or blood cells), tissues or other biological samples. Preferably, such sample is a nucleic acid preparation, e.g., a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (T) column contains RNA molecules with poly (A) tails. Those poly A+ RNA molecules could be mature mRNA, RNA processing intermediates, nascent transcripts or degradation intermediates.

Biological samples may be of any biological tissue or fluid or cells. Frequently the sample will be a "clinical sample" which is a sample derived from a patient. Clinical samples provide rich sources of information regarding the various states of genetic network or gene expression. Some embodiments of the invention are employed to detect mutations and to identify the function of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

In a preferred embodiment, the level of expression of a marker for oral cancer is assessed by detecting the presence of a nucleic acid corresponding to the marker in the sample. In another preferred embodiment, the level of expression of a marker for oral cancer is assessed by detecting the presence of a protein corresponding to the marker in the sample. In a preferred aspect, the presence of the protein is detected using a reagent which specifically binds to the protein, e.g., an antibody, an antibody derivative, and/or an antibody fragment.

Detection involves contacting a sample with a compound or an agent capable of detecting a marker associated with oral cancer such that the presence of the marker is detected in the biological sample. A preferred agent for detecting marker RNA is a labeled or labelable nucleic acid probe capable of hybridizing to marker RNA. The nucleic acid probe can be, for example, complementary to any of the nucleic acid markers of oral cancer disclosed herein, or a portion thereof, such as an oligonucleotide which specifically hybridizes marker RNA.

A preferred agent for detecting a marker protein is a labeled or labelable antibody capable of binding to the marker protein. Antibodies can be polyclonal, or more preferably, monoclonal. An intact antibody, antibody derivative, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The detection methods described herein can be used to detect marker RNA or marker protein in a biological sample in vitro as well as in vivo. In vitro techniques for detection of marker RNA include, but are not limited to, Northern hybridizations and in situ hybridizations. In vitro techniques for detection of marker protein include, but are not limited to, enzyme linked immunosorbent assays (ELISAs), Western blots, immunoprecipitations, and immunofluorescence assays. Alternatively, marker protein can be detected in vivo in a subject by introducing into the subject a labeled antibody against the marker protein. For example, the antibody can be labeled with a radioactive marker whose presence and location in a subject can be detected by standard imaging techniques.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNases are inhibited or destroyed by heat treatment followed by proteinase treatment.

Methods of isolating total mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In a preferred embodiment, total RNA is isolated from a given sample using, for example, an acid guanidiniumphenol-chloroform extraction method followed by polyA+ mRNA isolation by oligo dT column chromatography or by using (dT)n magnetic beads (see, e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987) each hereby incorporated by reference in their entireties for all purposes). See also PCT/US99/25200 for complexity management and other sample preparation techniques, which is hereby incorporated by reference in its entirety for all purposes.

Frequently, it is desirable to amplify the nucleic acid sample prior to hybridization. One of skill in the art will appreciate that methods of amplifying nucleic acids are well known in the art and that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. A high density array may then be performed which includes probes specific to the internal standard for quantification of the amplified nucleic acid.

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990)), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

Cell lysates or tissue homogenates often contain a number of inhibitors of polymerase activity. Therefore, the skilled practitioner typically incorporates preliminary steps to isolate total RNA or mRNA for subsequent use as an amplification template. One tube mRNA capture methods may be used to prepare poly(A)+ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra).

It will be appreciated by one of skill in the art that the direct transcription method described above provides an antisense RNA (aRNA) pool. Where aRNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., Gene, 88: 25–36 (1990)).

Other analysis methods that can be used in the present invention include electrochemical denaturation of double stranded nucleic acids, U.S. Pat. No. 6,045,996 and 6,033,850, the use of multiple arrays (arrays of arrays), U.S. Pat. No. 5,874,219, the use of scanners to read the arrays, U.S. Pat. Nos. 5,631,734; 5,744,305; 5,981,956 and 6,025,601, methods for mixing fluids, U.S. Pat. No. 6,050,719, integrated device for reactions, U.S. Pat. No. 6,043,080, integrated nucleic acid diagnostic device, U.S. Pat. No. 5,922,591, and nucleic acid affinity columns, U.S. Pat. No. 6,013,440. All of the above patents are hereby incorporated by reference in their entireties for all purposes.

Laser dissection microscopy is one method that can be used in the present invention. That technique is be shown in provisional application 60/182,452 which is hereby incorporated by reference in its entirety for all purposes. Other techniques include L. Zhang et al., Science 276, 1268 (1997), Mahadevappa, M. & Warrington, J. A. *Nat. Biotechnol.* 17, 1134–1136 (1999) and Luo, L. et al. *Nature Med.* 5, 117–122 (1999) which are all hereby incorporated by reference in their entireties for all purposes.

In a preferred embodiment, the invention provides methods of assessing the efficacy of test compounds and compositions for treating oral cancer. The methods entail identifying candidate or test compounds or agents (e.g., peptides, peptidomimetics, small molecules or other drugs) which have an inhibitory effect on oral cancer. Candidate or test compounds or agents which have an inhibitory effect on oral cancer are identified in assays that employ oral cancer cells, such as an expression assay entailing direct or indirect measurement of the expression of an oral cancer marker (e.g., a nucleic acid marker or a protein marker). For example, modulators of expression of oral cancer markers can be identified in a method in which a cell is contacted with a candidate compound and the expression of oral cancer markers (e.g., nucleic acid markers and/or protein markers) in the cell is determined. The level of expression of oral cancer markers in the presence of the candidate compound is compared to the level of expression of oral cancer markers in the absence of the candidate compound. The candidate compound can then be identified as a modulator of expression of oral cancer based on this comparison.

The invention also encompasses kits for assessing whether a subject is afflicted with oral cancer, as well as kits for assessing the presence of oral cancer cells. The kit may comprise a labeled compound or agent capable of detecting oral cancer markers (e.g., nucleic acid markers and/or protein markers) in a biological sample, a means for determining the amount of oral cancer markers in the sample, and a means for comparing the amount of oral cancer markers in the sample with a standard. The compound or agent can be packaged in a suitable container. The kit can further comprise instructions for using the kit to detect oral cancer markers.

Those skilled in the art will recognize that in a preferred embodiment, the expression profiles from the reference samples will be input to a database. A relational database is preferred and can be used, but one of skill in the art will recognize that other databases could be used. A relational database is a set of tables containing data fitted into pre-defined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. See U.S. Ser. No. 09/354,935, which is hereby incorporated by reference in its entirety for all purposes.

In one embodiment the invention matches the experimental sample to a database of reference samples. The database is assembled with a plurality of different samples to be used as reference samples. An individual reference sample in one embodiment will be obtained from a patient during a visit to a medical professional. The sample could be, for example, a tissue, blood, urine, feces or saliva sample. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases. One skilled in the art will also recognize that some of the indicators of status will be determined by less precise means, for example information obtained from a patient interview is limited by the subjective interpretation of the patient. Additionally, a patient may lie about age or lack sufficient information to provide accurate information about ethnic or other information. Descriptions of the severity of disease symptoms is a particularly subjective and unreliable indicator of disease status.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status, and one where the samples are grouped primarily by pharmacological status. Within each table the samples can be further grouped according to the two remaining categories. For example, the physiological status table could be further categorized according to disease and pharmacological status.

As will be appreciated by one of skill in the art, the present invention may be embodied as a method, data processing system or program products. Accordingly, the present invention may take the form of data analysis systems, methods, analysis software and etc. Software written according to the present invention is to be stored in some form of computer readable medium, such as memory, hard-drive, DVD ROM or CD ROM, or transmitted over a network, and executed by a processor. The present invention also provides a computer system for analyzing physiological states, levels of disease states and or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input.

U.S. Pat. No. 5,733,729 illustrates an example of a computer system that may be used to execute the software of an embodiment of the invention. This patent shows a computer system that includes a display, screen, cabinet, keyboard, and mouse. The mouse may have one or more buttons for interacting with a graphic user interface. The cabinet preferably houses a CD-ROM or DVD-ROM drive, system memory and a hard drive which may be utilized to store and retrieve software programs incorporating computer code that implements the invention, data for use with the invention and the like. Although a CD is shown as an exemplary computer readable medium, other computer readable storage media including a floppy disk, a tape, a flash memory, a system memory, and a hard drive may be utilized. Additionally, a data signal embodied in a carrier wave (e.g., in a network including the internet) may be the computer readable storage medium.

The patent also shows a system block diagram of a computer system used to execute the software of an embodiment of the invention. The computer system includes a monitor, a keyboard, and a mouse. The computer system further includes subsystems such as a central processor, a system memory, a fixed storage (e.g., a hard drive), a removable storage (e.g., CD-ROM), a display adapter, a sound card, speakers, and a network interface. Other computer systems suitable for use with the invention may include additional or fewer subsystems. For example, another computer system may include more than one processor or a cache memory. Computer systems suitable for use with the invention may also be embedded in a measurement instrument. The embedded systems may control the operation of, for example, a GENECHIP® Probe array scanner (also called a GENEARRAY® scanner sold by Agilent corporation, Palo Alto Calif.) as well as executing computer codes of the invention.

Computer methods can be used to measure the variables and to match samples to eliminate gene expression differences that are a result of differences that are not of interest. For example, a plurality of values can be input into computer code for one or more physiological, pharmacological and/or disease states. The computer code can thereafter measure the differences or similarities between the values to eliminate changes not attributable to a value of interest. Examples of computer programs and databases that can be used for this purpose are shown in U.S. Ser. Nos. 09/354,935, 08/828,952, 09/341,302, 09/397,494, 60/220587, and 60/220645, which are hereby incorporated by reference in their entireties for all purposes.

Computer software to analyze data generated by microarrays is commercially available from Affymetrix Inc. (Santa Clara) as well as other companies. Affymetrix Inc. distributes GENECHIP®, now known as MicroArray suite, LIMS, Microdb, Jaguar, DMT, and other software. Other databases can be constructed using the standard database tools available from Microsoft (e.g., Excel and Access).

High-density oligonucleotide arrays are particularly useful for monitoring the gene expression pattern of a sample. In one approach, total mRNA isolated from the sample is converted to labeled cRNA and then hybridized to an array such as a GENECHIP® oligonucleotide array. Each sample is hydridized to a separate array. Relative transcript levels are calculated by reference to appropriate controls present on the array and in the sample.

EXAMPLE I

Preparing Nucleic Acid Samples

Tissue samples were obtained from 5 patients as described in Table 1 below. Each of patients 1–5 has a history of smoking and alcohol consumption, which are the major etiological causes of oral cancer. Each patient exhibited squamous cell carcinoma (SCC): patient 1 was moderately differentiated, patients 2 and 3 were well differentiated, patient 4 was moderately differentiated and patient 5 was moderate to poorly differentiated. Normal tissue is designated as "A" and tumor tissue is designated as "B". the term "ppd" means packs per day and "cig" means either a cigarette or a cigar.

TABLE 1

| Identifier | Gender | Age | Smoking History | Alcohol Consumption |
|---|---|---|---|---|
| 1A, 1B | F | 80 | Not Known | Not Known |
| 2A, 2B | M | 61 | 2ppd/15 yrs | 2 shots/day |
| 3A, 3B | M | 68 | 1–2 ppd/40 yrs | 3 beers/day |
| 4A, 4B | M | 75 | 1–2 cig/day | 2 drinks/day |
| 5A, 5B | F | 60 | 40 pack/yr | Heavy |

Normal and tumor cells from a solid tumor site from within the oral cavity were obtained using laser capture microdissection as described in provisional application 60/182,452 which is hereby incorporated by reference in its entirety for all purposes. According to that method, biopsies were taken and snap frozen. The biopsies were sectioned at 5 microns and mounted on slides. They were then stained with hematoxylin and eosin. Laser capture microdissection was then used to procure malignant and normal keratinocytes. Laser capture microdissection, RNA isolation, IVT, 3 rounds of T7 RNA polymerase linear amplification, and probe biotinylation were carried out according to the methods of Alevizos et al., submitted, (2000) and Ohyama et al., Biotechniques 29, 530–6 (2000), each of which are hereby incorporated by reference in their entireties for all purposes. Basically, RNA was extracted and then cDNA synthesis was carried out using SUPERSCRIPT™ (Life Technologies). cRNA synthesis and labeling was carried out using Ampliscribe (Epicenter technology) and BioArray High Yield RNA Transcript Labeling System (Enzo).

The quality and quantity of isolated RNA was examined by reverse transcription polymerase chain reaction (RT-PCR) of five cellular maintenance gene transcripts of high to low abundance (glyceraldehyde-3-phosphate dehydrogenase, tubulin-α, β-actin, ribosomal protein S9, and ubiquitin C) (Ohyama et al., 2000). The quantity of isolated RNA was also assessed with RIBOGREEN® RNA Quantitation Reagent and kit (Molecular Probes, Eugene, Oreg.) using spectrofluorometry (Bio-Rad, Hercules, Calif.). Only those samples exhibiting PCR products for all five cellular maintenance genes were used for subsequent analysis. The biotinylated cRNA from the ten samples (five normal and five cancer) were further used to hybridize the Affymetrix Test-1 probe arrays to determine cRNA quality and integrity. The arrays contain probes representing a handful of maintenance genes and a number of controls (Ohyama et al., 2000). Analysis of the arrays confirmed the RT-PCR findings. cRNA linearly amplified from human oral cancer tissue produced no nonspecific or unusual hybridization patterns, and transcripts corresponding to the maintenance genes were detected. The 5' region of the RNA was degraded, but sufficient 3' transcript was intact to proceed with hybridization using the HuGeneFL probe arrays. In addition, probes synthesized on the arrays are biased to the last 600 bp in the 3' region of the transcripts. Yields of cDNA resulting from the LCM, RNA isolation, and after two rounds of T7 amplification are shown in FIG. 1A. Linear amplification of total RNA began with ~100 ng of total RNA. As shown in FIG. 1A, the amount of double stranded cDNA (ds-cDNA) after two rounds of T7 amplification is dependent on the quality of the LCM-generated RNA from the normal and tumor tissues.

FIG. 1B summarizes the hybridization outcome of the five paired cases of oral cancers. The percent transcript detected ranged from 26 to 40 percent, indicating satisfactory quality and representation of the harvested RNA. Note that the difference between the normal and cancer samples from each patient is very similar, indicating little variability among each pair, suggesting that the quality of the RNA isolated from the normal and tumor epithelium is similar.

EXAMPLE II

Analysis of Nucleic Acid Samples Using MicroArrays

The cRNA was fragmented as described by Wodicka et al. (1997) and then hybridized to Affymetrix probe arrays such as GENECHIP® Test 1, Human U95A and HuGeneFL probe arrays. Hybridization was carried out for a time period of between about 12 to 16 hours. All array washing, staining and scanning were carried out as described in the Gene Expression Manual (Affymetrix, Inc. 1999 hereby incorporated by reference in its entirety for all purposes). The Affymetrix arrays include probe sets consisting of oligonucleotides 25 bases in length. Probes are complementary to the published sequences (GENBANK®) as previously described (Lockhart et al., 1996). The sensitivity and reproducibility of the GENECHIP® probe arrays is such that RNAs present at a frequency of 1:100,000 are unambiguously detected, and detection is quantitative over more than three orders of magnitude (Redfern et al., 2000; Warrington et al., 2000). In this set of experiments with oral cancer samples, the bacterial transcript (BioB), spiked before the hybridization at concentration of 1.5 pM. This concentration, which corresponds to three copies per cell, based on the assumption that there are 300,000 transcripts per cell with an average transcript length of 1 kb, was defined as present in nine out of ten experiments (Lockhart et al., 1996). Array controls, and performance with respect to specificity and sensitivity are the same as those previously described (Lockhart et al., 1996; Mahadevappa & Warrington, 1999; Wodicka et al., 1997). Information regarding the genes represented on the arrays used in this experiment can be found at www.netaffx.com.

EXAMPLE III

Software Analysis of Data

The data obtained from the microarrays was analyzed using various methods and software commercially available and known to those skilled in the art. These methods and software include T-test, GENECHIP® software available from Affymetrix to perform a comparison analysis; GeneCluster SOM software to perform a cluster analysis, identify genes and develop characteristics of gene expression profiles; and MATLAB™ software to identify genes that are differentiating and to identify gene classes. Additional software that can be used to analyze chip data includes GenExplore and PCA.

For GeneCluster analysis and the computation of self organizing maps (SOM), gene expression levels and geometry of nodes were input into the GeneCluster software. Before the computation of the SOM, two preprocessing steps took place. First, a filter was applied to exclude genes that did not change significantly across the pairs. Genes were eliminated if they did not show a relative change of x=2 and an absolute change of y=35, (x, y)=(2, 35). Second, normalization of expression levels across experiments was carried out, thus emphasizing the expression pattern rather than the absolute expression values. Data was normalized using GENECHIP® software. A description of the normalization procedure can be found on pp. A5–14, GENECHIP® Expression Analysis Technical Manual, (Tamayo et al., 1999).

Differential gene expression using GENECHIP® analysis software revealed that 404 probe sets changed in the majority of the cases (⅗) (set forth in FIGS. 7A–7K). Among the 404, 211 were increased in tumor samples and 193 were decreased in tumor samples, compared to normal samples. As shown in FIG. 2A, 39 probe sets used allowed the detection of changes in gene expression in all five cases. Sixteen genes showed increased expression in tumor samples and 23 genes showed decreased expression in tumor samples, compared to normal samples. FIG. 2B is a list of differentially expressed genes grouped into biological pathways known to be relevant in carcinogenesis. FIG. 2C is a list of differentially expressed genes which are up regulated in tumor samples. FIG. 2D is a list of differentially expressed genes which are down regulated in tumor samples.

The data presented in FIGS. 2A and 2B shows that many known genes involved in neoplasia are differentially expressed in the five paired cases of oral cancer. Thus, these genes are markers associated with oral cancer. Further, the data indicates that the expression of members of known biological pathways are altered during oral carcinogenesis. These include genes which regulate metastatic and invasion pathways, transcription factors, oncogenes and tumor suppressor genes, and differentiation markers (FIG. 2B). Of particular importance are the differentially expressed genes that are not yet fully functionally characterized or genes that have not been studied by classic methods in head and neck/oral carcinogenesis. One such example is neuromedin U (Nmu), which is downregulated in five out of five tumors (Szekeres et al., 2000). Nmu is a poorly understood protein that manifests potent contractile activities on smooth muscle cells. Recently, two G-protein coupled receptors (NMU1 and NMU2) have been identified to interact with Nmu with nanomolar potency (Fujii et al., 2000; Raddatz et al., 2000). Surprisingly, Nmu is relevant in the development of oral malignancy and can function as a marker for carcinogenesis.

In order to validate the expression level data, three metastatic pathway genes whose expression are consistently altered in the five paired cases of oral cancer were selected. Real-time quantitative PCR (RT-QPCR) in conjunction with the TAQMAN® specific probe system or SYBR® Green system were used to validate the expression levels of interstitial collagenase (a member of the MMP's involved in metastasis), urokinase plasminogen activator (UPA, associated with metastasis) and cathepsin L (a member of the serine proteases). The cDNA product of the reverse transcription reaction was used as the template for the RT-QPCR reaction. For the RT-QPCR reaction, the iCycler IQ™ Real Time PCR detection system (Bio-Rad, Hercules, Calif.) was used with TAQMAN® specific probes and primers for Cathepsin, and SYBR® Green buffer and reagents (Perkin Elmer/Applied Biosystems Foster City, Calif., USA) for Urokinase Plasminogen Activator and Collagenase I (Heid et al., 1996).

For designing the specific primers and probes, PE/ABD Primer Express software as well as MACVECTOR® were used. Primer sequences used were:

Collagenase forward: 5'-ACACGGAACCCCAAGGACA-3' (SEQ ID NO:1)
Collagenase Reverse: 5'-GTTTTGTTGCCGGTGGTTTT-3' (SEQ ID NO:2)
UPA forward: 5'-GCACCATCAAACAAACCCCCTTAC-3' (SEQ ID NO:3)
UPA reverse: 5'-CAGACAGAAAAACCCCTGCCTG-3' (SEQ ID NO:4)
Cathepsin L forward: 5'-CAGTGTGGTTCTTGTTGGGCT-3' (SEQ ID NO:5)
Cathepsin L reverse: 5'-CTTGAGGCCCAGAGCAGTCTA-3' (SEQ ID NO:6)

The final PCR products were run on 2% minigel to ensure single product amplification during the PCR assay.

Comparison of the microarray and RT-QPCR data as shown in FIG. 3 revealed that they approximate each other. The slight observed discrepancy in the precise quantitation of the GENECHIP® and the RT-QPCR was due to the fact that a minute amount (ng) of LCM-generated total RNA was used for amplification followed by biotinylation and hybridization to the GENECHIP® microarrays. Using the same LCM-generated total RNA, the GENECHIP® data of three metastatic tumor genes was validated by real-time quantitative PCR (RT-QPCR). These two independent approaches yielded data which indicated a similar trend (FIG. 4). Both methods indicate that genes were upregulated from undetectable levels in the control to moderate abundance in the tumor cells. Similar results of GENECHIP® versus RT-QPCR correlation were previously used by Welsh et al. to validate candidates identified in an ovarian cancer study (Welch et al., 2001). The RT-QPCR data confirmed the upregulation and downregulation of selected candidates. Therefore, while there is discrepancy in the precise quantitation of GENECHIP® and RT-QPCR data of each sample, the overall trend and correlation are similar. The array data produces information about relative abundance that is accurate to within 1.5 to 2 fold (Lockhart et al., 1996; Redfern et al., 2000) providing information that allows binning of the transcript levels by low, low-medium, medium, medium-high or high abundance (Warrington et al., 2000a; Warrington et al., 2000b; Lockhart et al., 1996; Redfern et al., 2000).

The actual comparative data for collagenase is graphically depicted in FIG. 4. As presented in FIG. 3, similar data were obtained for UPA & cathepsin L. Other high and low genes including Neuromedin U, GST, cytochrome P450, ALDH-9, ALDH-10 and Wilm's tumor-related protein have also been validated.

The microarray data can be analyzed by pattern recognition (clustering) software to aid in deriving lists of genes that distinguish and characterize disease versus normal biopsies, thus shedding light on molecular genetic profiles and ultimately the mechanism of the disease under study. Techniques used for conducting hierarchical clustering analyses include self-organizing maps (SOM), Bayesian, hierarchical, and k-means. SOM was selected because of advantages in initial exploration of the data allowing the operator to impose partial structure on the clusters (Tamayo et al., 1999). Other advantages of SOM include good computational properties, computational speed and ease of implementation. SOM analysis was applied to the microarray data on the five paired cases of oral cancers. The clusters graphically represent gene expression patterns across all ten samples (normal and tumor), each cluster differing in gene number and grouping. This method provides a candidate set of genes whose differing expression activity can be used to distinguish normal and tumor cell behavior.

By SOM analysis using GeneCluster software, 178 transcripts were found to be differentially expressed between tumor and normal tissues. An important observation is that many of the differentially down-regulated genes are known to be important enzymes in the xenobiotic metabolic pathway (Jourenkova-Mironova et al., 1999; Katoh et al., 1999; Park et al., 1997; Sato et al., 1999). These include cytochrome c oxidase subunit Vb (coxVb), gamma-aminobutyraldehyde dehydrogenase, microsomal glutathione S-transferase (GST-II), aldehyde dehydrogenase 7 (ADH7), COX C VIII, ALDH8, EPH2 cytosolic epoxide hydrolase and ALDH10. Further data analysis revealed that other xenobiotic pathway genes, not included in this cluster, were also down-regulated in all five cases, suggesting perhaps a general downregulation of xenobiotic pathway genes during oral cancer development.

The xenobiotic pathway is of importance in the degradative metabolism of both foreign/native toxic and carcinogenic products. Phase I and II xenobiotic enzymes are two key sequential steps in the metabolism of toxic substances including alcohol and tobacco products. It is interesting to note that most of the five cases of oral cancer were from heavy smokers and drinkers. These data indicate that key regulatory events were altered in the xenobiotic pathways during oral carcinogenesis that may contribute to the increased susceptibility towards carcinogens such as tobacco and alcohol, the two major etiological factors for oral carcinogenesis.

Figure 5:
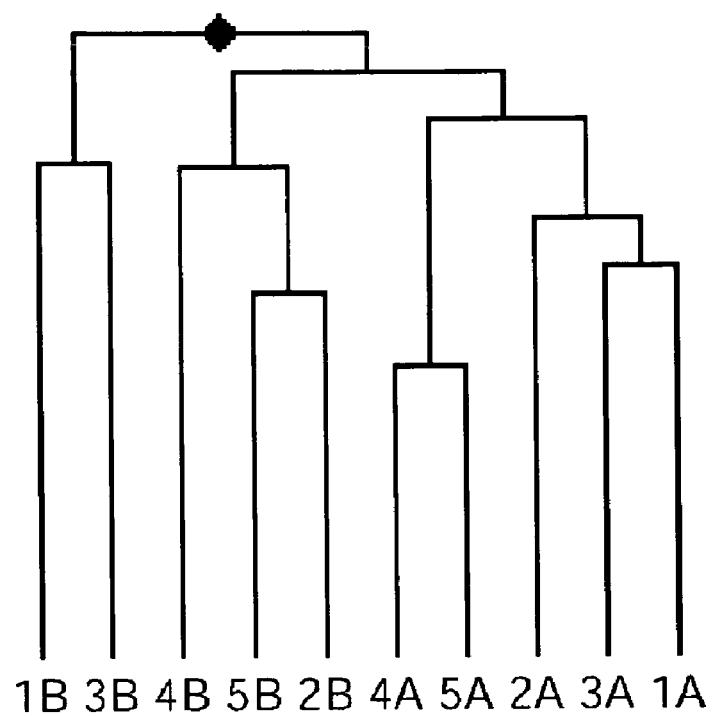
FIG. 5 shows hierarchical clustering.

Using MATLAB™ software analysis, 117 transcripts were identified to be differentially expressed between normal and tumor cells. Hierarchical clustering is shown in FIG. 5. The distinct clustering of the normal samples from the tumor samples suggests that LCM procured pure, homogenous samples.

Based on the outcome of three analytical methods (GENECHIP®, SOM and MATLAB™), ~600 candidate oral cancer genes were identified. Of this comprehensive set, 27 of the differentially expressed genes were identified by all three methods (set forth in FIG. 6). Of the 600 candidate genes, 41% were detected at low levels, 1–5 copies per cell.

EXAMPLE IV

Additional Studies

Shillitoe et al. and Leethanakul et al. have created expression libraries of human oral cancer cell lines and LCM-generated oral cancer tissues (Leethanakul et al., 2000a; Leethanakul et al., 2000b; Shillitoe et al., 2000). Their studies revealed 52 genes to be differentially expressed at >2-fold in at least three of the cancer tissue sets. Of these 52 genes, 26 were present on the Affymetrix GENECHIP®. Of these 26 overlapping genes, 18 were called absent (not detectable) in both normal and tumor samples (DP-2/U18422; TIMP-4/U76456; VEGF-C/U43142; FGF3/X14445; FGF5/M37825; FGF6/X63454; IGFBP5/M65062; EGF cripto protein CR1 and 2/M96956; APC/M74088; ERK6/X79483; GDI dissociation protein/U82532; MAP kinase p38/L35253; MKK6/U39657; MEKK3/U78876; Frizzled/L37782; FZD3/U82169; Dishevelled homolog/U46461; Patched homolog/U43148;); one gene showed no difference between normal and tumor tissues (cyclin H/U11791); one gene was upregulated in five out of five tumors (betal-catenin/X87838); three genes were upregulated in four out of five tumors (thrombospondin2 precursor/L12350; inhibitor of apoptosis protein/U45878; Caspase 5 precursor/U28014); one gene was upregulated in three out of five tumors (MMP-10/X07820); and one gene was down-regulated in four out of five tumors (RhoA/L25080). Finally, one gene was upregulated in two tumors, downregulated in two tumors, and called absent in the fifth oral cancer (TRAF2/U78798).

Of the 52 genes, two genes were detected present only through LCM/GENECHIP® analysis. They are human SPARC/osteonectin (J03040) and 5T4 oncofetal antigen (Z29083), which are consistently altered in the same manner in all five oral cancers examined.

Of interest is that a number of genes were identified by either LCM/oligonucleotide microarray approach or the LCM/cDNA library approach (Leethanakul et al., 2000a; Leethanakul et al., 2000b; Shillitoe et al., 2000) to be highly expressed/upregulated in oral cancer tissues. These include: ferritin heavy polypeptide I, urokinase plasminogen activator, ATP-binding cassette transporter, interleukin-1 receptor antagonist and keratin 4.

In addition, there are genes that were differentially expressed and detectable in the cell line study (Shillitoe et al., 2000), not in the Head and Neck CGAP (HNCGAP) libraries (Leethanakul et al., 2000a; Leethanakul et al., 2000b), but were detected present in the dataset. Examples of these genes are the collagen type 1 alpha 2 genes and the heat shock protein 70 kD gene. An example of a gene that was not identified by either LCM approach (HNCGAP libraries or the microarray method), but detected present in the cell line filtered cDNA microarray analysis is the transforming growth factor alpha gene, indicating the elevated expression of this gene maybe associated with in vitro culturing.

The different outcomes of the various studies are likely reflective of the experimental approaches and methods of analyses. First, by using LCM-generated RNA, contamination of heterogeneous cellular elements is avoided. Second, sample number and the type of microarray used in the respective studies may be relevant to the discrepancies. Third, the stage of the tumor, source and anatomical site of the oral cancers, and handling methods can further result in different gene expression levels. However, LCM-generated RNA, linearly amplified by T7 RNA polymerase and subsequently analyzed by high-density oligonucleotide GENE-CHIP® probe arrays impressively provided for the detection of 39 cellular genes consistently altered in five out of five different paired cases of human oral cancer making these genes useful as classifiers to predict the normal/malignant nature of oral epithelial tissues.

Importantly, the biology associated with these genes could be used to evaluate their role in oral cancer development. A number of these genes are secretory proteins that are upregulated in cancer tissues and could be evaluated as biomarkers of oral malignancy. These include osteonectin, ferritin, cathepsin L, proteoglycan (secretory granule) and oncofetal trophoblast glycoprotein.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of monitoring a gene expression profile associated with oral cancer comprising:
    contacting a first array of probes with a first population of nucleic acids derived from a human subject from one or more cells obtained from malignant oral tissue;
    contacting a second array of probes with a second population of nucleic acids derived from the human subject from one or more cells obtained from normal oral tissue; and
    determining relative hybridization of the first array of probes to the first population of nucleic acids relative to hybridization of the second array of probes to the second population of nucleic acids, wherein at least one nucleic acid that hybridizes differently is encoded by a gene of a gene expression profile that is associated with oral cancer, wherein the gene of the gene expression profile is selected from the group consisting of p-53 responsive gene 2, beta A inhibin, human alpha-1 collagen type I gene, placental protein 11, BENE protein, neuromedin U, flavin containing monooxygenase 2, runt-related transcription factor 1, alpha 2 collagen type I, fibrillin 1, absent in melanoma 1, nonvoltage-gated 1 alpha sodium channel, protein tyrosine kinase 6 and epithelial membrane protein 1.

2. A method of expression monitoring comprising:
    contacting a first array of probes with a first population of nucleic acids derived from at least one cell derived from normal oral tissue from a human subject;
    contacting a second array of probes with a second population of nucleic acids derived from at least one cell derived from malignant oral tissue from the human subject; and
    determining binding of the first array of probes to the nucleic acids from the first population relative to binding of the second array of probes to the nucleic acids from the second population to identify at least one probe binding to a nucleic acid that is differentially expressed between the first and second populations, wherein the nucleic acid is encoded by a gene selected from the group consisting of p-53 responsive gene 2, beta A inhibin, human alpha-1 collagen type I gene, placental protein 11, BENE protein, neuromedin U, flavin containing monooxygenase 2, runt-related transcription factor 1, alpha 2 collagen type I, fibrillin 1, absent in melanoma 1, nonvoltage-gated 1 alpha sodium channel, protein tyrosine kinase 6 and epithelial membrane protein 1.

3. A method of diagnosing a human subject with oral cancer, the method comprising:
    detecting a level of expression of a marker selected from a group of markers associated with oral cancer in a test sample from the human subject; and
    detecting the level of expression of the marker in a control sample from normal tissue from the human subject,
    wherein the level of expression of the marker in the control sample differs from the level of expression of the marker in the test sample when the subject is afflicted with oral cancer, and wherein the marker is encoded by a gene selected from p-53 responsive gene 2, beta A inhibin, human alpha-1 collagen type I gene, placental protein 11, BENE protein, neuromedin U, flavin containing monooxygenase 2, runt-related transcription factor 1, alpha 2 collagen type I, fibrillin 1, absent in melanoma 1, nonvoltage-gated 1 alpha sodium channel, protein tyrosine kinase 6 and epithelial membrane protein 1.

4. The method of claim 3, wherein the test sample from the subject comprises cells obtained from the subject.

5. The method of claim 4, wherein the cells are obtained from oral tissue.

6. The method of claim 4, wherein the cells are obtained from blood cells.

7. The method of claim 3, wherein the levels of expression of the marker in the control sample and in the test sample are assessed by a method comprising:
    contacting a first array of probes with a first population of nucleic acids derived from one or more cells from the test sample;
    contacting a second array of probes with a second population of nucleic acids derived from one or more cells from the control sample; and
    determining relative hybridization of the first array of probes to the first population of nucleic acids relative to hybridization of the second array of probes to the second population of nucleic acids.

8. The method of claim 7, wherein the first and second population of nucleic acids are RNA.

9. The method of claim 7, wherein the first and second population of nucleic acids are DNA.

10. The method of claim 7, wherein the first population of nucleic acids is amplified prior to contacting to the first array of probes or the second population of nucleic acids is amplified prior to contacting the second array of probes.

11. The method of claim 3, wherein the marker is a nucleic acid.

12. The method of claim 11, wherein the nucleic acid is RNA.

13. The method of claim 11, wherein the nucleic acid is DNA.

14. The method of claim 11, wherein one or more nucleic acids is amplified prior to assessing the sample.

15. A method for monitoring the progression of oral cancer in a human subject, the method comprising:
   detecting in a first sample obtained from the human subject at a first point in time, a level of expression of a marker selected from a group of markers associated with oral cancer;
   detecting in a subsequent sample obtained from the human subject at a subsequent point in time, the level of expression of the marker, and
   comparing the level of expression detected in the first and subsequent detecting samples in order to monitor the progression of oral cancer, wherein the marker is encoded by a gene selected from p-53 responsive gene 2, beta A inhibin, human alpha-1 collagen type I gene, placental protein 11, BENE protein, neuromedin U, flavin containing monooxygenase 2, runt-related transcription factor 1, alpha 2 collagen type I, fibrillin 1, absent in melanoma 1, nonvoltage-gated 1 alpha sodium channel, protein tyrosine kinase 6 and epithelial membrane protein 1.

16. The method of claim 15, wherein the first and the subsequent samples comprise cells obtained from the subject.

17. The method of claim 16, wherein the cells are obtained from oral tissue.

18. The method of claim 16, wherein the cells obtained are blood cells.

19. The method of claim 3, wherein the control sample from the subject comprises cells obtained from the subject.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Amplification primer

<400> SEQUENCE: 1
acacggaacc ccaaggaca                                              19

<210> SEQ ID NO 2
<211> LENGTH: 20
<212> TYPE: DNA
<213> ORGANISM: Artificial Sequence
<220> FEATURE:
<223> OTHER INFORMATION: Amplification primer

<400> SEQUENCE: 2
gttttgttgc cggtggtttt                                             20

<210> SEQ ID NO 3
<211> LENGTH: 24
<212> TYPE: DNA
<213> ORGANISM: Artificial Sequence
<220> FEATURE:
<223> OTHER INFORMATION: Amplification primer

<400> SEQUENCE: 3
gcaccatcaa acaaacccccc ttac                                       24

<210> SEQ ID NO 4
<211> LENGTH: 22
<212> TYPE: DNA
<213> ORGANISM: Artificial Sequence
<220> FEATURE:
<223> OTHER INFORMATION: Amplification primer

<400> SEQUENCE: 4
cagacagaaa aacccctgcc tg                                          22

<210> SEQ ID NO 5
<211> LENGTH: 21
<212> TYPE: DNA
<213> ORGANISM: Artificial Sequence
<220> FEATURE:
<223> OTHER INFORMATION: Amplification primer

<400> SEQUENCE: 5
cagtgtggtt cttgttgggc t                                           21
```

```
<210> SEQ ID NO 6
<211> LENGTH: 21
<212> TYPE: DNA
<213> ORGANISM: Artificial Sequence
<220> FEATURE:
<223> OTHER INFORMATION: Amplification primer

<400> SEQUENCE: 6
cttgaggccc agagcagtct a                                              21
```